United States Patent
Hazel et al.

(10) Patent No.: US 10,702,555 B2
(45) Date of Patent: *Jul. 7, 2020

(54) STABLE NEURAL STEM CELLS COMPRISING AN EXOGENOUS POLYNUCLEOTIDE CODING FOR A GROWTH FACTOR AND METHODS OF USE THEREOF

(71) Applicant: Neuralstem, Inc., Germantown, MD (US)

(72) Inventors: Thomas Hazel, North Potomac, MD (US); Karl K. Johe, Hallandale Beach, FL (US)

(73) Assignee: NEURALSTEM, INC., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,959

(22) Filed: Jun. 16, 2017

(65) Prior Publication Data

US 2017/0319625 A1 Nov. 9, 2017

Related U.S. Application Data

(63) Continuation of application No. 14/886,272, filed on Oct. 19, 2015, now Pat. No. 9,750,769.

(60) Provisional application No. 62/147,950, filed on Apr. 15, 2015, provisional application No. 62/066,174, filed on Oct. 20, 2014.

(51) Int. Cl.
| | |
|---|---|
| *C12N 5/22* | (2006.01) |
| *A61K 35/30* | (2015.01) |
| *A61K 38/30* | (2006.01) |
| *C12N 5/0797* | (2010.01) |
| *C12N 5/079* | (2010.01) |
| *C12N 5/10* | (2006.01) |
| *A61K 48/00* | (2006.01) |
| *C07K 14/65* | (2006.01) |

(52) U.S. Cl.
CPC .............. *A61K 35/30* (2013.01); *A61K 38/30* (2013.01); *A61K 48/00* (2013.01); *C12N 5/0618* (2013.01); *C12N 5/0623* (2013.01); *C12N 5/10* (2013.01); *C07K 14/65* (2013.01)

(58) Field of Classification Search
CPC .. C12N 5/0618; C12N 5/0623; C12N 5/0662; C12N 15/63; C12N 15/79; C12N 2510/04; C07K 14/475
See application file for complete search history.

(56) References Cited

U.S. PATENT DOCUMENTS

| | | |
|---|---|---|
| 4,753,635 A | 6/1988 | Sagen et al. |
| 4,980,174 A | 12/1990 | Sagen et al. |
| 5,082,670 A | 1/1992 | Gage |
| 5,093,317 A | 3/1992 | Lewis et al. |
| 5,166,065 A | 11/1992 | Williams et al. |
| 5,175,103 A | 12/1992 | Lee et al. |
| 5,411,883 A | 5/1995 | Boss et al. |
| 5,580,777 A | 12/1996 | Bernard et al. |
| 5,589,376 A | 12/1996 | Anderson et al. |
| 5,612,211 A | 3/1997 | Wilson et al. |
| 5,672,499 A | 9/1997 | Anderson et al. |
| 5,693,482 A | 12/1997 | Anderson et al. |
| 5,750,376 A | 5/1998 | Weiss et al. |
| 5,753,505 A | 5/1998 | Luskin |
| 5,753,506 A | 5/1998 | Johe |
| 5,770,414 A | 6/1998 | Gage et al. |
| 5,824,489 A | 10/1998 | Anderson et al. |
| 5,843,780 A | 12/1998 | Thomson |
| 5,849,553 A | 12/1998 | Anderson et al. |
| 5,851,832 A | 12/1998 | Weiss et al. |
| 5,928,947 A | 7/1999 | Anderson et al. |
| 5,932,473 A | 8/1999 | Swiderek et al. |
| 5,958,767 A | 9/1999 | Snyder et al. |
| 5,981,165 A | 11/1999 | Weiss et al. |
| 6,040,180 A | 3/2000 | Johe |
| 6,071,889 A | 6/2000 | Weiss et al. |
| 6,284,539 B1 | 9/2001 | Bowen et al. |
| 6,294,346 B1 | 9/2001 | Weiss et al. |
| 6,399,369 B1 | 6/2002 | Weiss et al. |
| 6,497,872 B1 | 12/2002 | Weiss et al. |
| 6,498,018 B1 | 12/2002 | Carpenter |
| 6,531,464 B1 | 3/2003 | Szabo et al. |
| 6,699,871 B2 | 3/2004 | Edmondson et al. |
| 7,101,709 B2 | 9/2006 | Weiss et al. |
| 7,115,418 B2 | 10/2006 | Weiss et al. |
| 7,361,505 B1 | 4/2008 | Weiss et al. |
| 7,833,513 B2 | 11/2010 | de la Monte |
| 2002/0107273 A1 | 8/2002 | Nakao et al. |
| 2003/0059369 A1 | 3/2003 | Kung et al. |
| 2005/0148069 A1 | 7/2005 | Gage et al. |
| 2007/0042437 A1 | 2/2007 | Wands et al. |
| 2009/0136465 A1 | 5/2009 | Merenick et al. |

FOREIGN PATENT DOCUMENTS

| | | |
|---|---|---|
| EP | 0 233 838 | 8/1987 |
| WO | WO 89/03872 | 5/1989 |

(Continued)

OTHER PUBLICATIONS

Lunn et al., "Autocrine Production of IGF-1 Increases Stem Cell-Mediated Neuroprotection," Stem Cells, Apr. 23, 2015, vol. 33, Iss. 5, pp. 1480-1489.

(Continued)

*Primary Examiner* — Robert C Hayes
(74) *Attorney, Agent, or Firm* — Morgan, Lewis & Bockius LLP; Christopher J. Betti

(57) ABSTRACT

The present disclosure provides a human neural stem cell comprising an exogenous polynucleotide coding for a growth factor such as IGF-1. Also disclosed are methods of using the human neural stem cells for the treatment of neurodegenerative diseases or disorders including, for example, ALS.

2 Claims, 10 Drawing Sheets

Specification includes a Sequence Listing.

(56) References Cited

FOREIGN PATENT DOCUMENTS

| WO | WO 90/06757 | 6/1990 |
| --- | --- | --- |
| WO | WO91/02003 | 2/1991 |
| WO | WO91/09936 | 7/1991 |
| WO | WO 91/17242 | 11/1991 |
| WO | WO 93/01275 | 1/1993 |
| WO | WO 93/09802 | 5/1993 |
| WO | WO 94/02593 | 2/1994 |
| WO | WO 94/03199 | 2/1994 |
| WO | WO 94/04675 | 3/1994 |
| WO | WO 94/10292 | 5/1994 |
| WO | WO 95/13364 | 5/1995 |
| WO | WO 96/09543 | 3/1996 |
| WO | WO 96/15226 | 5/1996 |
| WO | WO 98/48001 | 10/1998 |
| WO | WO 99/01159 | 1/1999 |
| WO | WO 99/11758 | 3/1999 |
| WO | WO 00/17323 | 3/2000 |
| WO | 2005/030932 A2 | 4/2005 |
| WO | WO 2006/055685 | 5/2006 |
| WO | 2013/070796 A2 | 5/2013 |
| WO | 2014/138003 A1 | 9/2014 |

OTHER PUBLICATIONS

Oishi et al., "Selective induction of neocortical GABAergic neurons by the PDK1-Akt pathway through activation of Mash 1," Proceedings of the National Academy of Sciences of the United States of America, Aug. 4, 2009, vol. 106, No. 31, pp. 13064-13069.

Park S. et al., "Growth factor-expressing human neural progenitor cell grafts protect motor neurons but do not ameliorate motor performance and survival in ALS mice," 2009, Experimental and Molecular Medicine, vol. 41, No. 7, pp. 487-500.

Ahmed, S. et al., "BDNF Enhances the Differentiation but Not the Survival of CNS Stem Cell-Derived Neuronal Precursors," The Journal of Neuroscience, 15(8): 5765-5778 (1995).

Almazan, et al., "Epidermal Growth and Bovine Growth Hormone Stimulate Differentiation and Myelination of Brain Cell Aggregates in Culture," Developmental Brain Research, 21:257-264, (1985).

Almazan, G., et al., "Triiodothyronine Stimulation of Oligodendroglial Differentiation and Myelination", Dev. Neurosci, 7:45-54, (1985).

Anchan, R.M., et al., "EFG and TGF-a Stimulate Retinal Neuroepithelial Cell Proliferation In Vitro", Neuron, 6:923-936, (1991).

Arsenijevic, Y., et al., "Isolation of multipotent neural precursors residing in the cortex of the adult human brain", Experimental Neurology, 170:48-62, (2001).

Avellana-Adalid, V., et al., "Expansion of Rat Oligodendrocyte Progenitors into Proliferative "Oligospheres" that Retain Differentiation Potential", Journal of neuroscience Research, 45:558-570, (1996). http://www3.interscience.wiley.com/cgi-bin/abstract/67559/ ABSTRACT.

Baas, P.W. et al., "Polarity orientation of microtubules in hippocampal neurons: Uniformity in the axon and nonuniformity in the dendrite," Proc. Natl. Acad. Sci. USA, vol. 85, pp. 8335-8339 (1988).

Bartlett P. F., "Regulation of Neural Precursor Differentiation in the Embryonic and Adult Forebrain," Clinical and Experimental Pharmacology and Physiology, vol. 22, p. 559-562, 1995.

Bartlett, P.F., et al., "Immortalization of mouse neural precursor cells by the c-myc oncogene", Neurobiology, 85:3255-3259, (1988).

Behl, C., "Apoptosis and Alzheimer's disease", Journal of Neural transmission, 107:1325-1344, (2000).

Bernard, O., et al., "Role of the c-myc and the N-myc Proto-Oncogenes in the Immortalization of Neural Precursors", Journal of Neuroscience Research, 24:9-20, (1989).

Bersano et al., "Clinical Studies in Stem Cells Transplantation for Stroke: A Review," Current Vascular Pharmacology, 2010, 8, 29-34.

Birren, S.J., et al., "A v-myc-Immortalized Sympathoadrenal Progenitor Cell Line in Which Neuronal Differentiation Is Initiated by FGF but Not NGF", Neuron, 4:189-201, (1990).

Bjerkvig et al., "Reaggregation of Fetal Rat Brain Cells in a Stationary Culture System I: Methodology and Cell Identification," In Vitro Cellular & Development Biology, 22:4 180-192 (1986).

Bredesen, D.E., et al., "Neural Transplantation Using Temperature-sensitive Immortalized Neural Cells: A Preliminary Report", Annals of Neurology, 27:205-207, (1990).

Bremner, J.D., et al., "Hippocampal volume reduction in major depression" Am. J. Psychiatry, 157:115-117, (2000).

Brezun, J., et al., "Depletion in serotonin decreases neurogenesis in the dentate gyrus and the subventricular zone of adult rats", Neuroscience, 89:999-1002, (1999).

Broe, M., et al., "Relationship between DNA fragmentation, morphological changes and neuronal loss in Alzheimer's disease and dementia with Lewy bodies", Acta Neuropathol, 101:616-624, (2001).

Brüstle O., et al., "Neuronal progenitors as tools for cell replacement in the nervous system," Neurobiology 1996, 6:688-695.

Brüstle O., et al., "Embryonic Stem Cell-Derived Glial Precursors: A Source of Myelinating Transplants", Science, 285:754-756, (1999).

Calhoun, John D. et al., "Differentiation of rhesus embryonic stem cells to neural progenitors and neurons," Biochemical and Biophysical Research Communications, 2003, vol. 306, pp. 191-197.

Calof, A.L., et al., "Analysis of neurogenesis in a mammalian neuroepithelium: proliferation and differentiation of an olfactory neuron precursor in vitro", Neuron, 3:115-127, (1989).

Cambray-Deakin, M.A., "The expression of excitatory amino acid binding sites during neuritogenesis in the developing rat cerebellum", Biol Abstr, 90:78577, (1990).

Cameron, H.A., et al., "Regulation of neurogenesis by growth factors and neurotransmitters", Journal of Neurobiology, 36:287-306, (1998).

Cao, Q., et al., "Stem Cell Repair of Central Nervous System Injury", Journal of Neuroscience Research, 68:501-510, (2002).

Carpenter, M.K., et al., "Generation and Transplantation of EGF-Responsive Neural Stem Cells Derived from GFAP-hNGF Transgenic Mice", Experimental Neurology, 148:187-204, (1997).

Carpenter, M.K., et al., "In Vitro Expansion of a Multipotent Population of Human Neural Progenitor Cells", Experimental Neurology, 158:265-278, (1999).

Carpenter reexamination U.S. Appl. No. 90/008,862 (reexamination of U.S. Pat. No. 6,103,530) entitled "Cultures of Human CNS Neural Stem Cells," filed Oct. 2, 2007.

Castillo, S.O., et al., "Dopamine Biosynthesis Is Selectively Abolished in Substantia Nigra/Ventral Tegmental Area but Not in Hypothalamic Neurons in Mice with Targeted Disruption of the Nurr1 Gene", Molecular and Cellular Neuroscience, 11:36-46, (1998).

Castillo, S.O., et al., "Organization, Sequence, Chromosomal Localization, and Promoter Identification of the Mouse Orphan Nuclear Receptor Nurr1 Gene", Genomics, 41:250-257, (1997).

Cattaneo, E., et al., "Proliferation and differentiation of neuronal stem cells regulated by nerve growth factor", Letters to Nature, 347:762-765, (1990).

Cepko, C.L., "Immortalization of Neural Cells Via Retrovirus-Mediated Oncogene Transduction", Annu. Rev. Neurosci., 12:47-65, (1989).

Chabot, P., "Transient expression of an intermediate filament-associated protein (IFAPa-400) during in vivo and in vitro differentiation of chick embryonic cells derived form neuroectoderm", Biol Abstr, 90:78577, (1990).

Chen et al., PLoS ONE (2001) vol. 6, pp. 1-10.

Cizkova et al., "Functional Recovery in Rats with Ischemic Paraplegia After Spinal Grafting of Human Spinal Stem Cells," Neuroscience, Jun. 29, 2007; 147(2): 546-560.

Conover, J.C. et al., "Ciliary neurotrophic factor maintains the pluripotentiality of embryonic stem cells," Development 119, 559-565 (1993).

Coon, H.G., et al., "Cell cultures of neuroblasts from rat olfactory epithelium that show odorant responses", Neurobiology, 86:1703-1707, (1989).

Coppell, A.L., et al., "Bi-phasic change in BDNF gene expression following antidepressant drug treatment", Neuropharmcaology, 44:903-910, (2003).

(56) References Cited

OTHER PUBLICATIONS

Cummings, B.J., et al., "Human Neural Stem Cells Differentiate and Promote Locomotor Recovery in Spinal Cord-Injured Mice", Proceedings of the National Academy of Sciences of the United States of America, 102(39):14069-14074, (2005).
Czeh, B., et al., "Stress-induced changes in cerebral metabolites, hippocampal volume, and cell proliferation are prevented by antidepressant treatment with tianepine", PNAS, 98:12796-12801, (2001).
Daadi et al., "Adherent Self-Renewable Human Embryonic Stem Cell-Derived Neural Stem Cell Line: Functional Engraftment in Experimental Stroke Model," Plos ONE, Feb. 2008, vol. 3, Issue 2: e1644.
Dahlstrand et al., "Nestin mRNA expression correlates with the central nervous system progenitor cell state in many, but not all, regions of developing central nervous system," Developmental Brain Research 84:109-129 (1995).
Davis, A., et al., "A self-renewing multipotential stem cell in embryonic rat cerebral cortex", Letters to Nature, 372:263-266, (1994).
DiCicco-Bloom, E., et al., "Neuroblast Mitosis in Dissociated Culture: Regulation and Relationship to Differentiation", The Journal of Cell Biology, 110:2073-2086, (1990).
Doering et al., "Isolation and identification of neuroblast precursor cells from mouse neopallium," Developmental Brain Research 5:229-233 (1982).
Drago, J., et al., "A Method for the Isolation of Purified Murine Neuroepithelial Cells From the Developing Mouse Brain", Journal of Neuroscience Methods, 37:251-256, (1991).
Drago, J., et al., "Basic Fibroblast Growth Factor Upregulates Steady-State Levels of Laminin B1 and B2 Chain mRNA in Cultured Neuroepithelial Cells", Experimental Cell Research, 196:246-254, (1991).
Drago, J., et al., "Fibroblast Growth Factor-Mediated Proliferation of Central Nervous System Precursors Depends on Endogenous Production of Insulin-like Growth Factor I", Neurobiology, 88:2199-2203, (1991).
Drago, J., et al., "Laminin through its Long Arm E8 Fragment Promotes the Proliferation and Differentiation of Murine Neuroepithelial Cells in Vitro", Experimental Cell Research, 192:256-265, (1991).
D'Sa, C. et al., "Antidepressants and neuroplasticity", Bipolar Disorders, 4:183-194, (2002).
Dutton, G.R., "Isolation, Culture, and Use of Viable Central nervous System Perikarya", Methods in Neuroscience, 2:87-102, (1990).
Eccleston et al., "Requirements for Brain Cell Attachment, Survival and Growth in Serum-Free Medium: Effects of Extracellular Matrix, Epidermal Growth Factor and Fibroblast Growth Factor" Dev. Neurosci 7:308-322 (1985).
Ehrlich, M.E., et al., "DARPP-32 development in the caudate nucleus is independent of afferent input from the substantia nigra", Biol. Abstr. vol. 90(78577), (1990).
Eilers, M., et al., "Chimaeras of Myc oncoprotein and steroid receptors cause hormone-dependent transformation of cells", Letters to Nature, 340:66-68, (1989).
Engebraaten et al., "Effects of EGF, bFGF, and NGF and PDGF(bb) on cell proliferative, migratory and invasive capacities of human brain-tumor biopsies in vitro," Int. J. Cancer, 53:209-214 (1993).
Eriksson, P.S., et al., "Neurogenesis in the adult human hippocampus", Nature Medicine, 4:1313-1317, (1998).
Escary, J. et al., " Leukaemia inhibitory factor is necessary for maintenance of haematopoietic stem cells and thymocyte stimulation," Nature, vol. 363, pp. 361-364 (1993).
European Office Action dated Apr. 17, 2014, for corresponding European Appln. No. 05851748.3.
Evans, R.M., "The Steroid and Thyroid Hormone Receptor Superfamily," Science, vol. 240, pp. 889-895 (1988).
Evrard, C. et al., "Immortalization of bipotential and plastic glio-neuronal precursor cells," Proc. Natl. Acad. Sci. USA, vol. 87, pp. 3062-3066 (1990).
Falk, A., et al., "Amphiregulin is a mitogen for adult neural stem cells", Journal of Neuroscience Research, 69:757-762, (2002).

Feldman, D. H., et al., "Differentiation of Ionic Currents in CNS Progenitor Cells: Dependence upon Substrate Attachment and Epidermal Growth Factor," Experimental Neurology 140, 206-217 (1996).
Feron, F., et al., "Stress induces neurogenesis in non-neuronal cell cultures of adult olfactory epithelium", Neuroscience, 88:571-583, (1999).
Finger, S., et al., "Nimodipine and Neural Grafts", Duke Med. Cent. Lib., 34(1'2):208, (1991).
Finley, M. et al., "Synapse Formation and Establishment of Neuronal Polarity by P19 Embryonic Carcinoma and Embryonic Stem Cells," The Journal of Neurosciences, 16(3): 1056-1065 (1996).
Fischer, A.J., et al., "Exogenous Growth Factors Induce the Production of Ganglion Cells at the Retinal Margin", Development, 129:2283-2291, (2002).
Flax J.D., et al., "Engraftable human neural stem cells respond to developmental cues, replace neurons and express foreign genes", Nature Biotechnology, 16:1033-1039, (1998).
Frappaz, D., et al., "Enhancement of Growth of Primary Metastatic Fresh Human Tumors of the Nervous system by Epidermal Growth Factor in Serum-free Short Term Culture", Neurosurgery, 23:355-359, (1988).
Frederiksen, K. et al., "Immortalization of Precursor Cells from the Mammalian CNS," Neuron, vol. 1, 439-448 (1988).
Fröjdö et al., "Culturing and characterization of astrocytes isolated from juvenile rainbow trout (*Oncorhynchus mykiss*)," Comparative Biochemistry and Physiology Part A, 133, (2002) 17-28.
Fujiwara, Y., et al., "Intravenously Injected Neural Progenitor Cells of Transgenic Rats Can Migrate to the Injured Spinal Cord and Differentiate Into Neurons Astrocytes and Oligodendrocytes", Neuroscience Letters, 366(3):287-291, (2004).
Gage, F.H., et al., "Isolation, Characterization, and use of Stem Cells From the CNS", Annu. Rev. Neurosci.,18:159-192, (1995).
Gage, F.H. et al., "Survival and differentiation of adult neuronal progenitor cells transplanted to the adult brain," Proc. Natl. Acad. Sci., vol. 92, pp. 11879-11883, Dec. 1995.
Gatica, et al., "Polylysine-containing peptides, including the carboxyl-terminal segment of the human c-Ki-ras 2 protein, affect the actvity of some key membrane enzymes," Proceedings of the National Academy of Sciences of USA, 1987, vol. 84, pp. 324-328.
Glasky, et al., "Update: Central and Peripheral Nervous Systems AIT-082, a novel purine derivative with neuroregenerative properties", Exp. Opin. Invest. Drugs, 6:1413-1417, (1997).
Godfraind, C. et al., "In Vivo Analysis of Glial Cell Phenotypes during a Viral Demyelinating Disease in Mice," The Journal of Cell Biology, vol. 109, pp. 2405-2416 (1989).
Goldman, S.A., et al., "In vitro neurogenesis by neuronal precursor cells derived from the adult songbird brain", The Journal of Neuroscience, 12:2532-2541, (1992).
Gould, E., et al., "Inaugural Article: Adult-generated hippocampal and neocortical neurons in macaques have a transient existence", PNAS, 98:10910-10917, (2001).
Green, S., et al., "Human oestrogen receptor cDNA: sequence, expression and homology to v-erb-A", Nature, 320:134-139, (1986).
Gritti, A., et al., "Multipotential Stem Cells from the Adult Mouse Brain Proliferate and Self-Renew in Response to Basic Fibroblast Growth Factor", The Journal of Neuroscience, 16:1091-1100, (1996).
Gu W. et al., "Cortical neurogenesis in adult rats after reversible photothrombotic stroke", Journal of Cerebral Blood Flow and Metabolism, vol. 20, pp. 1166-1173, 2000.
Guentert-Lauber, B. et al., "Responsiveness of Astrocytes in Serum-Free AggregateCultures to Epidermal Growth Factor: Dependence on the Cell Cycle and the Epidermal Growth Factor Concentration," Dev. Neurosci. 7: 286-295 (1985).
Hall, et al., "An Introduction to Molecular Neurobiology", p. 357, 1992.
Hata, M., et al., "A decrease in the wet-dog shakes response to the second administration of kainic acid in juvenile rats", Biol. Abstr., 92(31832), (1991).
Hauser, K.F., et al., "Opioids intrinsically inhibit the genesis of mouse cerebellar granule neuron precursors in vitro: differential

(56) References Cited

OTHER PUBLICATIONS impact of mu and delta receptor activation on proliferation and neurite elongation", European Journal of Neuroscience, 12:1291-1293, (2000).
Hermanson, M., et al., "PDGF and its receptors following facial nerve axotomy in rats: expression in neurons and surrounding glia", Exp. Brain Res., 102:415-422, (1995).
Hockfield et al., "Identification of Major Cell Classes in the Developing Mammalian Nervous System," The Journal of Neuroscience 5:12 3310-3328 (1985).
Hollenberg et al., "Epidermal Growth Factor: Receptors in Human Fibroblasts and Modulation of Action by Cholera Toxin," Proc. Nat. Acad. Sci. USA, vol. 70, No. 10, pp. 2964-2968, Oct. 1973.
Honegger, P., et al., "Growth and Differentiation of Aggregating Fetal Brain Cells in a Serum-Free Defined Medium", Nature, 282:305-308, (1979).
Honkaniemi, J., et al., "Focal brain injury induces multiple immediate early genes encoding zinc finger transcription factors", Molecular Brain Research, 28:157-163, (1995).
Horcholle-Bossavit, G., et al., "Postnatal development of peroneal motoneurons in the kitten", Biol. Abstr., 90(78577), (1990).
Horner et al., "Regenerating the damaged central nervous system," Nature, vol. 407, Oct. 26, 2000, pp. 963-970.
Hoshimaru, M., et al., "Differentiation of the immortalized adult neuronal progenitor ce line HC2S2 into neurons by regulatable suppresision of the v-myc oncogene", Proc. Natl. Acad., 93:1518-1523, (1996).
Howland, et al., "Focal loss of the glutamate transporter EAAT2 in a transgenic rat model of SODI mutant-mediated amyotrophic lateral sclerosis (ALS)", PNAS, 99:1604-1609, (2002).
Hunter, S.F., et al., "Growth factor responses of enriched bipotential glial progenitors", Biol. Abstr., 90(78577), (1990).
Isacson, O., "The production and use of cells as therapeutic agents in neurodegenerative diseases," The Lancet Neurology, 2:417-424, (2003).
Ishibashi, et al., "Human Neural Stem/Progenitor Cells, Expanded in Long-Term Neurosphere Culture, Promote Functional Recovery After Focal Ischemia in Mongolian Gerbils", Journal of Neuroscience Research, 78:215-223, (2004).
Jain, M., et al., "GABAergic Immunoreactivity is Predominant in Neurons Dervied From Expanded Human Neural Precursor Cells In Vitro", Experimental Neurology, 182(1):113-123, (2003).
Jablonska et al., Acta Neurobiol Exp. (2011) vol. 71, pp. 74-85.
Jelitai, M., et al., "Regulated appearance of NMDA Receptor Subunits and Channel Functions Duriing In Vitro Neuronal Differentiation", Journal of Neurobiology, 51:54-65, (2002).
Jin, K., et al., "Stem cell factor stimulates neurogenesis in vitro and in vivo", The Journal of Clinical Investigation, 110:311-319, (2002).
Jin, K., et al., "Vascular endothelial growth factor (VEGF) stimulates neurogenesis in vitro and in vivo", PNAS, 99:11946-11950, (2002).
Johe, K. et al., "Single factors direct the differentiation of stem cells from the fetal and adult central nervous system," Genes & Development, vol. 10, pp. 3129-3140, 1996.
Jones-Villeneuve, et al., "Retinoic Acid Induces Embryonal Carcinoma Cells to Differentiate into Neurons and Glial Cells", The Journal of Cell Biology, 94:253-262, (1982).
Jung, et al., "Novel pluripotential neural progenitor lines exhibiting rapid controlled differentiation to neurotransmitter receptor-expressing neurons and glia," Eur. J. Neuroscj., vol. 10 pp. 3246-3256 (1998).
Kalladka et al., Neurochem.Int. (2011), doi:I O. 1016/j.neuint.2011.03.016, 4 pages.
Kehl, L.J., et al., "Neurogenesis in postnatal rat spinal cord: a study in primary culture", Science, 276:586-589, (1997).
Kempermann, G., et al., "Depressed new neurons-adult hippocampal neurogenesis and a cellular plasticity hypothesis of major depression", Biological Psychiatry, 54:499-503, (2003).
Kempermann, G., et al., "Genetic determinants of adult hippocampal neurogenesis correlate with acquisition, but not probe trial performance, in the water maze task", European Journal of Neuroscience, 16:129-136, (2002).
Kershaw, T.R., et al., "Foetal H-2Kb-tsA58 Transgenic Mouse Tissue Develops in a Similar Manner to ISO Geneic Foetal Tissue when Transplanted into Adult Mouse Brain", Duke Med. Cent. Lib., 34(4):208, (1991).
Kilpatrick, et al., "Cloning and Growth of Multipotential Neural Precursors: Requirements for Proliferation and Differentiation", Neuron, 10:255-265, (1993).
Kilpatrick, T.J., Richards, L.J., and Bartlett, P.F., "The Regulation of Neural Precursor Cells within the Mammalian Brain," Mol. Cell. Neurosci., 6, 2-15, (1995).
Kilpatrick, T.J., and Bartlett, P.F., "Cloned Multipotential Precursors from the Mouse Cerebrum Require FGF-2, Whereas Glial Restricted Precursors Are Stimulated with Either FGF-2 or EGF," J. Neurosci., 15(5):3653-3661 (1995).
Kitani, H., et al., "Isolation and Characterization of Mouse Neural Precursor Cells in Primary Culture", In Vitro Cell. Dev. Biol., 27A:615-624, (1991).
Kuhn, H.G., et al., "Neurogenesis in the dentate gyns of the adult rat: age-related decrease of neuronal progeneitor proliferation", The Journal of Neuroscience, 16:2027-2033, (1996).
Kumar, et al., "Localisation of the oestradiol-binding and putative DNA-binding domains of the human oestrogen receptor," The EMBO Journal, vol. 5, No. 9, pp. 2231-2236, (1986).
Law et al., "Identification of New Brain-Specific Transcription Factor, NURR 1," Molecular Endocrinology, pp. 2129-2135, 1992.
Law, et al., "Molecular Cloning of a Novel Member of theNuclear Receptor Superfamily Realted to the Orphan Receptor, TR2," Gene Expr., vol. 4, pp. 77-84, (1994).
Lee, et al., The v-myconcogene, Oncogene, 18:2997-3003, (1999).
Lee, A.L., et al., "Stress and depression: possible links to neurons death in the hippocampus", Bipolar Disorders, 4:117-128, (2002).
Lee, J., et al., "Dietary restriction increases the number of newly generated neural cells, and induces BDNF expression, in the dentate gyrus of rats", Journal of Molecular Neuroscience, 15:99-108, (2001).
Lendahl et al., "CNS Stem Cells Express a New Class of Intermediate Filament Protein," Cell 60:585-595 (1990).
Lepore, A.C., et al., "Neural Precursor Cells Can be Delivered Into the Injured Cervical Spinal Cord by Intrathecal Injection at the Lumbar Cord", Brain Research, 1045(1-2):206-216, (2005).
Lichtenwalner, R.J., et al., "Intracerebroventricular infusion of insulin-like growth factor-I ameliorates the age-related decline in hippocampal neurogenesis", Neuroscience, 107:603-613, (2001).
Lindvall, et al., "Stem cell therapy for human neurodegenerative disorders—how to make it work," Nature Med., 10:S42-S50, (2004).
Ling, et al., "Differentiation of Mesencephalic Progenitor Cells into Dopaminergic Neurons by Cytokines," Exp. Neurol., 149, 411-423, (1998).
Littlewood, T.D., et al., "A modified oestrogen receeptor ligan-binding domain as an improved switch for the regulation of heterologous proteins". Nucleic Acids Research. 1995, vol. 23, No. 10, pp. 1686-1690, see abstract.
Llado, J. et al., "Neural Stem Cells Protect Against Glutamate-Induced Excitotoxicity and Promote Survival of Injured Motor Neurons Thrrough the Secretion of Neurotrophic Factors," Molecular and Cellular Neurosciences, 27(3):322-331, (2004).
Lois, et al., "Proliferating subventricular zone cells in the adult mammalian forebrain can differentiate into neuros and glia," Proc. Nat'l Acad. Sci., 90:274-2077, (1993).
Lovejoy, D.A., et al., "Primary structure of two forms of gonadotropin-releasing hormone from brains of the American alligator", Biol. Abstr., 92(31832), (1991).
Lu et al., "Neural stem cells constitutively secrete nerotrophic factors and promote extensive host axonal growth after spinal cord injury," Experimental Neurology 181 (2003) 115-129.
Lucassen, P.J., et al., "Hippocampal apoptosis in major depression is a minor event and absent from subareas at risk for glucocorticoid overexposure", American Journal of Pathology, 158:453-468, (2001).
Lumsden, A. et al., "Patterning the Vertibrate Neuraxis," Science, vol. 274, pp. 1109-1115, Nov. 15, 1996.

(56) References Cited

OTHER PUBLICATIONS

Lyman, W.D., et al., "Human Fetal Central Nervous System Organotypic Cultures", Developmental Brain Research, 60:155-160, (1991).
Ma, W., et al., "Acetylcholine stimulates cortical precursor cell proliferation in vitro via muscarinic receptor activation and MAP kinase phosphorylation", European Journal of Neuroscience, 12:1227-1240, (2000).
Madsen, T.M., et al., "Increased neurogenesis in a model of electroconvulsive therapy", Biological Psychiatry, 47:1043-1049, (2000).
Mages, H. et al., "NOT, A Human Immediate-Early Response Gene Closely Related to the Steroid/Thyroid Hormone Receptor NAK1/TR3," Molecular Endocrinology, p. 1583-1591, 1994.
Malberg, J.E., et al., "Chronic antidepressant treatment increases neurogenesis in adult rat hippocampus", The Journal of Neuroscience, 20:9104-9110, (2000).
Marin, N., et al., "0.-amyloid-induced activation of caspase-3 in primary cultures of rat neurons", Mechanisms of Ageing and Development, 119:63-67, (2000).
Marsala, M., et al., "Spinal Implantation of hNT Neurons and Neuronal Precursors: Graft Survival and Functional Effects in Rats With Ischemic Spastic Paraplegia", European Journal of Neuroscience, 20(9):2401-2414, (2004).
Martz et al., "The Role of Cell-cell Contact in "Contact" Inhibition of Cell Division: A Review and New Evidence," J. Cell. Physiol., 79:189-210, (1971).
Masters, B.A., "Insulin-like growth factor I (IFG-I) receptors and IGF-I action in oligodendrocytes from rat brains", Biol. Abstr., 92(31832), (1991).
Mattson, M.P., "Stem cells as therapeutics for neurodegenerative disorders?" Expert Rev. Neurotherapeutics, 267-273, (2001).
Mauerhoff, T. et al., "Differential Expression and Regulation of Major Histocompatibility Complex (MHC) Products in Neural and Glial Cells of the Human Fetal Brain", Journal of Neuroimmunology, 18:271-289, (1988).
Mayo, W., et al., "Pregnenolone sulfate and aging of cognitive functions: behavioral, neurochemical, and morphological investigations", Hormones and Behavior, 40:215-217, (2001).
McCarthy, M., et al., "Infection of Human Neural Cell Aggregate Cultures with a Clinical Isolate of Cytomegalovirus", Journal of Neuropathology and Experimental Neurology, 50:441-450, (1991).
McConnell, S., "Constructing the Cerebral Cortex: Neurogenesis and Fate Determination," Neuron, vol. 15, 761-768, Oct. 1995.
McKay, R., et al., "Mechanisms Regulating Cell number and Type in the Mammalian Central Nervous System", Cold Spring Harbor Symposia on Quantitative Biology, LV:291-301, (1990).
McKay, R., et al., "Stem Cells in the Developing and Adult Brain," (abs.) (1995).
McKay, R., et al., "Stem Cells in the Central Nervous System," Science, 276, pp. 66-71 (1997).
Mervaala, E., et al., "Quantitative MRI of the hippocampus and amygdala in severe depression", Psychological Medicine, 30:117-125, (2000).
Monnet-Tschudi, F. et al. "Influence of Epidermal Growth Factor on the Maturation of Fetal Rat Brain Cells in Aggregate Culture," Dev Neurosci 1989, vol. 11, pp. 30-40.
Morrison, R.S., et al., "Trophic Stimulation of Cultured Neurons from Neonatal Rat Brain by Epidermal Growth Factor", Science, 238:72-75, (1987).
Morrison, S.J., et al., "Regulatory Mechanisms in Stem Cell Biology," Cell, vol. 88,287-298, Feb. 7, 1997
Morshead et al., "Postmitotic Death Is the Fate of Constitutively Proliferating Cells in the Subependymal Layer of the Adult Mouse Brain," The Journal of Neuroscience 12(1):249-256 (1992).
Morshead et al., "Neural Stem Cells in the Adult Mammalian Forebrain: A Relatively Quiescent Subpopulation of Subependymal Cells," Neuron 13:1071-1082 (1994).
Murphy, M., et al., "Fibroblast Growth Factor Stimulates the Proliferation and Differentiation of Neural Precursor Cells In Vitro", Journal of Neuroscience Research, 25:463-475, (1990).

Murrell, W., et al., "Neurogenesis in adult human," NeuroReport, 7:1189-1194, (1996).
Mytilineou, C., et al., "Epidermal Growth Factor-Induced Survival and Proliferation of Neuronal Precursor Cells from Embryonic Rat Mesencephalon", Neuroscience Letters, 135:62-66, (1992).
Naegele et al., "Recent Advancements in Stem Cell and Gene Therapies for Neurological Disorders and Intractable Epilepsy." Neuropharmacology, May 2010; 58(6): 855-864.
Nakafuku, et al., "Establishment and Characterization of a Multipotential Neural Cell Line That Can Conditionally Generate Neurons, Astrocytes, and Oligodendrocytes In Vitro", Journal of Neuroscience Research, 41:153-168, (1995).
Nakagawa, S., et al., "Regulation of neurogenesis in adult mouse hippocampus by cAMP and the cAMP reponse element-binding protein", The Journal of Neuroscience, 22:3673-3682, (2002).
Nestler, E.J., et al., "Neurobiology of Depression", Neuron, 34:13-25, (2002).
Nibuya, M., et al., "Chronic antidepressant administration increases the expression of cAMP response element binding protein (CREB) in rat hippocampus", The Journal of Neuroscience, 16:2365-2372, (1996).
Nielsen, F.C., et al., "Receptor Binding, Endocytosis, and Mitogenesis of Insulin-Like Growth Factors I and II in Fetal Rat Brain Neurons", Journal of Neurochemistry, 56:12-21, (1991).
Nolte, J., "Introduction to the Nervous System," The Human Brain an Introduction to Its Functional Anatomy, Fourth Edition pp. 1-35 (1999).
Ohkura, et al., "Structure, mapping and expression of a human NOR-1 gene, the third member of the Nur77/NGFI-B family," Biochim. Biophys. Acta, 1308:205-214, (1996).
Oka, S., et al, "Autologous Transplantation of Expanded Neural Precursor Cells Into the Demyelinated Monkey Spinal Cord", Brain Research, 1030(1):94-102, (2004).
Okabe, et al., "cDNA Cloning of a NGFI-B/nur77-Related Transcription Factor from an Apoptotic Human T Cell Line," J. Immunol., 154:3871-3879, (1995).
Okano, et al., "Neural stem cells and regeneration of injured spinal cord", Kidney International, 68:1927-1931, (2005).
Okano, H., "Neural stem cells: progression of basic research and perspective for clinical application," Keio Journal of Medicine, vol. 51, pp. 115-128, 2002.
Palmer T D. et al., "The Adult Rat Hippocampus Contains Primordial Neural Stem Cells," Molecular and Cellular Neuroscience 8, 389-404 (1997).
Palmer T D. et al., "Fibroblast growth factor-2 activates a latent neurogenic program in neural stem cells from diverse regions of the adult CNS," The Journal of Neuroscience, vol. 19, pp. 8487-8497, 1999.
Park K. et al., "Global gene and cell replacement strategies via stem cells," Gene Therapy, vol. 9, pp. 613-624, 2002.
Pena de Ortiz et al., "HZF-3, an immediate-early orphan receptor homologous to NURR1/NOT: Induction upon membrane depolarization and seizures," Mol. Brain Res. 38:1-13 (1996).
Perrone-Capano et al., "Epigenetic factors and midbrain dopaminergic neurone development," Bioessays vol. 18 No. 10 pp. 817-824 (1996).
Peterson D. A. et al., "Trophic factor therapy for neuronal death," Alzheimer Disease, 2nd Edition, Chapter 25, pp. 373-388, 1999.
Pham, K. et al., "Repeated restraint stress suppresses neurogenesis and induces biphasic PSA-NCAM expression in the adult dentate gyrus," European Journal of Neuroscience, vol. 17, pp. 879-886, 2003.
Piescinski, P. et al., "Neurogenesis of the amygdaloid complex in the rhesus monkey," Society for Neuroscience Abstracts, vol. 16, p. 1147, 1990.
Pincus D W. et al., "In vitro neurogenesis by adult human epileptic temporal neocortex," Clinical Neurosurgery, Chapter 2, pp. 17-25.
Politis, BMC Medicine (2010) 8:80., 5 pages).
Pollerberg et al., "Generation of Cell Lines From Embryonic Quail Retina Capable of Mature Neuronal Differentiation," Journal of Neuroscience Research, vol. 41, pp. 427-442, 1995
Price, "Brain Stems," Current Biology 5:3 232-234 (1995).

(56) References Cited

OTHER PUBLICATIONS

Pucilowski, 0. et al., "Decreased hyperthermic effect of MK801 in selectively bred hypercholinergic rats," Ref. No. 31832, Biol Abstr vol. 92, 1991.
Pulliam, L. et al., "A Normal Human Brain Cell Aggregate Model for Neurobiological Studies," Journal of Neuroscience Research, vol. 21, pp. 521-230, 1988.
Qian, X et al., "FGF2 Concentration Regulates the Generation of Neurons and Glia from Multipotent Cortical Stem Cells," Neuron, vol. 18, pp. 81-93, Jan. 1997.
Qu, T. et al., "Human neural stem cells improve cognitive function of aged brain," NeuroReport, vol. 12, pp. 1127-1132, 2001.
Raina, A K. et al., "Abortive apoptosis in Alzheimer's disease," Acta Neuropathol, vol. 101, pp. 305-310, 2001.
Rajan et al., "Neural Stem Cells and Their Munipulation," (2006) Methods in Ezymol. 419:23-52.
Rakic, P. "Radial Versus Tangential Migration of Neuronal Clones in the Developing Cerebral Cortex," Proc. Natl. Acad. Sci, USA, vol. 92, pp. 11323-11327, Dec. 1995.
Rao et al., "Immortalization and Controlled In Vitro Differentiation of Murine Multipotent Neural Crest Stem Cells," (1997) J. Neurobiol. 32, 722.
Rappa, G. et al., "Efficient Expansion and Gene Transduction of Mouse Neural Stem/Progenitor Cells on Recombinant Fibronectin," Neuroscience, 2004, vol. 124, pp. 823-830.
Rathbone M P. et al., "Trophic effects of purines in neurons and glial cells," Progress in Neurobiology, vol. 59, pp. 663-690, 1999.
Ray, J. and Gage, F.H., "Spinal Cord Neuroblasts Proliferate in Response to Basic Fibroblast Growth Factor," J. Neurosci. 14(6): 3548-3564 (1994).
Ray, J. Peterson, D., Schinstine, M. & Gage, F., "Proliferation, differentiation, and long-term culture of primary hippocampal neurons," Proc. Natl. Acad. Sci. USA vol. 90, pp. 3602-3606 (1993).
Redies et al., "Differentiation and Heterogeneity in T-Antigen Immortalized Precursor Cell Lines From Mouse Cerebellum," Journal of Neuroscience Research 30:601-615 (1991).
Reichmann et al., "Activation of an Inducible c-FosER Fusion Protein Causes Loss of Epithelial Polarity and Triggers Epithelial-Fibroblastoid Cell Conversion," (1992) Cell vol. 71, pp. 1103-1116.
Renoncourt et al., Neurons derived in vitro from ES cells express homeoproteins characteristic of motoneurons and interneurons (1998) Mechanisms of Development 79 pp. 185-197.
Resnick, J et al., "Long-term proliferation of mouse primordial germ cells in culture," Nature, vol. 359, pp. 550-551, Oct. 8, 1992.
Rettig, W.J. et al., "Cell Type-specific Control of Human Neuronectin Secretion by Polypeptide mediators and Phorbol Ester," The Journal of Histochemistry and Cytochemistry, vol. 37, pp. 1777-1786, 1989.
Rettig, W.J. et al., "Stimulation of Human Neuronectin Secretion by Brain-Derived Growth Factors," Brain Research, vol. 487, pp. 171-177, 1989.
Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.
Reynolds, B.A. et al., "A Non-Transformed, Growth Factor Dependent Stem Cell Line Derived From the Embryonic Mouse CNS Produces Neurons, Astrocytes and Oligodendrocytes," Duke Med Cent Lib 34.P3, p. 208, 1991.
Reynolds, B.A. et al., "EGF- and TGFα-responsive striatal embryonic progenitor cells produce both neurons and astrocytes," Society for Neuroscience Abstracts, vol. 16, p. 1147, 1990.
Reynolds, B.A. et al., "Generation of Neurons and Astocytes from Isolated Cells of the Adult Mammalian Central Nervous System," Science, vol. 255, pp. 1707-1709, 1992.
Reynolds, B.A. et al., "Clonal and Population Analyses Demonstrate That an EGF-Responsive Mammalian Embryonic CNS Precursor Is a Stem Cell," Developmental Biology 175, 1-13 (1996).
Righi et al., myc-Immortalized Microglial Cells Express a Functional Platelet-Activating Factor Receptor (1995) J. Neurochem. 64, 121-129.

Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Cardiotrophin-1 with Tetanus Toxin," The Journal of Neuroscience, vol. 25, pp. 539-549, 2005.
Romand, R. et al., "Development of tonotopy oin the inferior colliculus: 1. Electrophysiological mapping in house mice," Ref. No. 78577. Biol Abstr vol. 90, 1990.
Roth, K. A., "Caspases, apoptosis, and Alzheimer disease: causation, correlation, and confusion," Journal of Neuropathology and Experimental Neurology, vol. 60, pp. 829-838, 2001.
Rothstein J.D. et al., " Decreased Glutamate Transport by the Brain and Spinal Cord in Amyotrophic Lateral Sclerosis," The New England Journal of Medicine, vol. 326, pp. 1464-1468, 1992.
Roy N S, et al., "In vitro neurogenesis by progenitor cells isolated from the adult human hippocampus," Nature Medicine, vol. 6, pp. 271-277, 2000.
Rozental R. et al., "Differentiation of hippocampal progenitor cells in vitro: temporal expression of intercellular coupling and voltage- and ligand-gated responses," Developmental Biology, vol. 167, pp. 350-362, 1995.
Rudland, P.S. et al., "Growth Control in cultured Mouse Fibroblasts: Induction of the Pleiotypic and Mitogenic Responses by a Purified Growth Factor," Proc. Nat. Acad. Sci., vol. 71, No. 7, pp. 2600-2604, Jul. 1974.
Rutka, J.T. et al., "Characterization of Fetal Human Brain Cultures," Dev. Neurosci., vol. 9, pp. 154-173, 1987.
Ryder et al., "Establishment and Characterization of Multipotent Neural Cell Lines Using Retrovirus Vector-Mediated Oncogene Transfer," (1990) J. Neurobiol vol. 21, No. 2, pp. 356-375.
Sabate, O., Horellou, P., Vigne, E., Colin, P., Perricaudet, M., Buc-Caron, M.-H. & Mallet, J., "Transplantation to the rat brain of human neural progenitors that were genetically modified using adenoviruses," Nature Genetics 9, 256-260 (1995).
Sah et al., "Bipotent progenitor cell lines from the human CNS," (1997) Nature Biotech. 15:574.
Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.
Santarelli, L. et al., "Requirement of hippocampal neurogenesis for the behavioral effects of antidepressants," Science, vol. 301, pp. 805-809, 2003.
Sato, H. et al., "Somatostatin receptors in the senescent rat brain: A quantitative autoradiographic study," Ref. No. 31832, Biol Abstr vol. 92, 1991.
Satoh M. et al., "Promotion of neurogenesis in mouse olfactory neuronal progenitor cells by leukemia inhibitory factor in vitro," Neuroscience Letters, vol. 225, pp. 165-168, 1997.
Saucedo-Cardenas et al., "Cloning and structural organization of the gene encoding the murine nuclear receptor transcription factor, NURR1," Gene 187:135-139 (1997).
Saucedo-Cardenas et al., "Nurr1 is essential for the induction of the dopaminergic phenotype and the survival of ventral mesencephalic late dopaminergic precursor neurons," Proc. Natl. Acad. Sci. USA 95:4013-4018 (1998).
Scearce et al., "RNR-1, a Nuclear Receptor in the NGFI-B/Nur77 Family That Is Rapidly Induced in Regenerating Liver," J. Biol. Chem. vol. 268, No. 12, pp. 8855-8861 (1993).
Schapira, A., "Pathogenesis of Parkinson's disease," Bailliere's Clin. Neurol. vol. 6, No. 1, pp. 15-36 (1997).
Schinstine, M. et al., "Expression of Neuronal Antigens by Astrocytes Derived from EGF-Generated Neuroprogenitor Cells," Experimental Neurology 141, 67-78 (1996).
Schlaggar, B.L. et al., "Potential of Visual Cortex to Develop an Array of Functional Units Unique to Somatosensory Cortex," Science, vol. 252, pp. 1556-1560 (1991).
Scott B W. et al., "Neurogenesis in the dentate gyms of the rat following electroconvulsive shock seizures," Experimental Neurology, vol. 165, pp. 231-236, 2000.

(56) References Cited

OTHER PUBLICATIONS

Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.
Seigel, G.M. et al., "Differentiation of oncogenically altered chick neuroretinal cells by succinylated concanavalin A," Society for Neuroscience Abstracts, vol. 16, p. 1147, 1990.
Selvakumarun et al., "Myeloblastic Leukemia Cells Conditionally Blocked by Myc-Estrogen Receptor Chimeric transgenes for Terminal Differentiation Coupled to Growth Arrest and Apoptosis," (1993) Blood vol. 81, No. 9, pp. 2257-2262.
Shihabuddin et al., "Adult Spinal Cord Stem Cells Generate Neurons after Transplantation in the Adult Dentate Gyrus," The Journal of Neuroscience, Dec. 1, 2000, 20(23): 8727-8735.
Shingo T. et al., "Erythropoietin regulates the in vitro and in vivo production of neuronal progenitors by mammalian forebrain neural stem cells," The Journal of Neuroscience, vol. 21, pp. 9733-9743, 2001.
Shirayama, Y. et al., "Brain-derived neurotrophic factor produces antidepressant effects in behavioral models of depression," The Journal of Neuroscience, vol. 22, pp. 3251-3261, 2002.
Shors T J. et al., "Neurogenesis in the adult is involved in the formation of trace memories," Nature, vol. 410, pp. 372-376, 2001.
Shou J. et al., "BMPs inhibit neurogenesis by a mechanism involving degradation of a transcription factor," Nature Neuroscience, vol. 2, pp. 339-345, 1999.
Sigma-Aldrich, Material Safety Data Sheet for Ethylenediaminetetraacetic Acid, for Complexometry, pp. 1-7 (1995).
Silani, V. et al., "Human Neuronal Cells in Culture: From Concepts to Basic Methodology," Boll. 1st. Sieroter. Mila., vol. 69, pp. 309-313, 1990.
Snyder et al., "Taking Stock and Planning for the Next Decade: Realistic Prospects for Stem Cell Therapies for the Nervous System," (2004) J. Neurosci. Res. 76:157-168.
Sorensen, K.A. et al., "Postembryonic neurogenesis in the Brain of Manduca Sexta," Society for Neuroscience Abstracts, vol. 16, p. 1147, 1990.
Stemple, D. et al., "Neural Stem Cells Are Blasting Off," Neuron, vol. 18, Jan. 1-4, 1997.
Sternfeld, M.D. et al., "Cultured Human Retinal Pigment Epithelial Cells Express Basic Fibroblast Growth Factor and its Receptor," Current Eye Research, vol. 8, pp. 1029-1037, 1989.
Stewart, J.S. et al., "Olfactory bulb and sensory epithelium in goldfish: Morphological alterations accompanying growth," Ref. No. 78577. Biol Abstr vol. 90, 1990.
Stone et al., "Definition of Regions in Human c-mycThat Are Involved in Transformation and Nuclear Localization," Molecular and Cellular Biology vol. 7, No. 5, pp. 1697-1709, 1987.
Svendsen, C.N. & Rosser, A.E., "Neurones from stem cells?" Trends in Neuroscience vol. 18, No. 11, pp. 465-466 (1995).
Svendsen, C.N., Fawcett, J.W., Bentlage, C. & Dunnett, S.B., "Increased survival of rat EGF-generated CNS precursor cells using B27 supplemented medium," Exp. Brain Res. 102: 407-414 (1995).
Svendsen, C.N. et al., "Survival and Differentiation of Rat and Human Epidermal Growth Factor-Responsive Precursor Cells Following Grafting into the Lesioned Adult Central Nervous System," Experimental Neurology 137, 376-388 (1996).
Svendsen, C.N. et al., "A new method for the rapid and long term growth of human neural prescursor cells," Journal of Neuroscience Methods 85 (1998) 141-152.
Takahashi J. et al., "Retinoic acid and neurotrophins collaborate to regulate neurogenesis in adult-derived neural stem cell cultures," J Neurobiol, vol. 38, pp. 65-81, 1999.
Takahashi, T. et al., "Cell cycle kinetics of the E14 murine cerebral ventricular zone: estimates based upon S-Phase labeling with BUdR," Society for Neuroscience Abstracts, vol. 16, p. 1147, 1990.
Takeichi, M. et al., "Roles of Magnesium and Calcium Ions in Cell-to-Substrate Adhesion," Experimental Cell Research 74 (1972) 51-60.

Taupin P, et al., "FGF-2-responsive neural stem cell proliferation requires CCg, a novel autocrine/paracrine cofactor," Neuron, vol. 28, pp. 385-397, 2000.
Taylor, M. et al., "Induction of Differentiation of Rat Retinal, Germinal, Neuroepithelial Cells by dbcAMP," Journal of Neurobiology, vol. 21, pp. 470-481, 1990.
Temple, S., "Division and Differentiation of Isolated CNS Blast Cells in Microculture," Nature, vol. 340, pp. 471-473-1989.
Temple, S. et al., "Vertebrate neural progenitor cells: subtypes and regulation," Neurobiology 1996, 6:11-17.
Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.
Tohyama et al., "Nestin Expression in Embryonic Human Neuroepithelium and in Human Neuroepithelial Tumor Cells," Laboratory Investigation 66:3 303-313 (1992).
Torelli, S. et al., "Human Fetal Brain Cultures: A Model to Study Neural Proliferation, Differentiation and Immunocompetence," Adv. Exp. Med. Biol, vol. 296, pp. 121-134, 1991.
Torres, R.A. et al., "Alteration of Neuronal Regulation of Astrocytoma Proliferation by Insertional Mutagenesis," Society for Neuroscience Abstracts, vol. 16, p. 1147, 1990.
Trenkner et al., "Cell Reaggregation and Migration, Fiber and Synapse Formation," The Journal of Cell Biology 75:915-940 (1977).
Tropepe, V. et al., "Direct Neural Fate Specification from Embryonic Stem Cells: A Primitive Mammalian Neural Stem Cell Stage Acquired through a Default Mechanism," Neuron, vol. 30, 65-78, Apr. 2001.
Turner M.R. et al., "Abnormal cortical excitability in sporadic but not homozygous D90A SOD I ALS," J Neurol Neurosurg Psychiatry, vol. 76, pp. 1279-1285, 2005.
Unsicker et al., "Growth factor function in the development and maintenance of midbrain dopaminergic neruons: concepts, facts and prospects for TGF-β," Ciba Found. Symp. 196, pp. 70-84 (1996.
Usvald et al., "Analysis of Dosing Regimen and Reproducibility of Intraspinal Grafting of Human Spinal Stem Cells in Immunosuppressed Minipigs," Cell Transplantation, vol. 19, Issue 9, pp. 1103-1122, Apr. 2010.
Van Praag et al., "Running enhances neurogenesis, learning, and long-term potentiation in mice," PNAS, vol. 96, pp. 13427-13431, 1999.
Van Praag et al., "Running increases cell proliferation and neurogenesis in the adult mouse dentate gyrus," Nature Neuroscience, vol. 2, pp. 266-270, 1999.
Vescovi et al., "Isolation and Cloning of Multipotential Stem Cells from the Embryonic Human CNS and Establishment of Transplantable Human Neural Stem Cell Lines by Epigenetic Stimulation," (1999) Exp. Neurol. 156, 71-83.
Vescovi, A.L., Reynolds, B.A., Fraser, D.D., and Weiss, S., "bFGF Regulates the Proliferative Fate of Unipotent (Neuronal) and Bipotent (Neuronal/Astroglial) EGF-Generated CNS Progenitor Cells," Neuron vol. 11, pp. 951-966 (1993).
Vicario-Abejon, C., Johe, K., Hazel, T., Collazo, D. & McKay, R., "Functions of Basic Fibroblast Growth Factor and Neurotrophins in the Differentiation of Hippocampal Neurons," Neuron vol. 15, 105-114 (1995).
Villa, A. et al., "Intracellular calcium ion stores in chicken purkinje neurons; Differential distribution of the low affinity-high capacity calcium binding protein, calsequestrin, of calcium ATPase and of the ER luminal protein," Bip. Ref. No. 31832, Biol Abstr vol. 92, 1991.
Von Frijtag, J. C. et al., "Chronic imipramine treatment partially reverses the !nog-term changes of hipocampal synaptic plasticity in socially stressed rats," Neuroscience Letters, vol. 309, pp. 153-156, 2001.
Von Visger, J.R. et al., "Differentiation and Maturation of Astrocytes Derived from Neuroepithelial Progenitor Cells in Culture," Experimental Neurology 128: 34-40, 1994.
Vu, E.T. et al., "Evidence for a Computational Distinction Between Proximal and Distal Neuronal Inhibition," Science, vol. 255, pp. 1710-1712, 1992.

(56) References Cited

OTHER PUBLICATIONS

Wachs et al., "High Efficacy of Clonal Growth and Expansion of Adult Neural Stem Cells," Laboratory Investigation, Jul. 2003, vol. 83, No. 7, pp. 949-962.

Wagner et al, "Induction of a midbrain dopaminergic phenotype in Nurr1-overexpressing neural stem cells by type 1 astrocytes," 1999, Nat. Biotech., vol. 17:, pp. 653-659.

Wainer, B.H. et al., "In vitro cell cultures as model of the basal forebrain," Adv Exp Med Biol., vol. 295, pp. 415-437, 1991.

Wang et al., "A regulatory system for use in gene transfer," (1994) PNAS vol. 91, pp. 8180-8184.

Wang et al., "Induction of dopaminergic neurono phenotype in the midbrain by Sonic hedgehog protein," Nature Medicine, vol. 1, pp. 1184-1188, 1995.

Watanabe, R.T. et al., "Rod Photoreceptor development in vitro: intrinsic properties of proliferating neuroepithelial cells change as development proceeds in the rat retina," NeuralCulture, Abstract, 1990.

Watt et al., "Nucleotide sequence of cloned cDNA of human c-myc oncogene," Nature 303: 725-728, 1983.

Weiss et al., "Multipotent CNS Stem Cells Are Present in the Adult Mammalian Spinal Cord and Ventricular Neuroaxis," The Journal of Neuroscience, vol. 16, pp. 7599-7609, 1996.

Weiss et al. reexamination U.S. Appl. No. 90/008,580 (reexamination of U.S. Pat. No. 5,851,832) entitled "In Vitro Growth and Proliferation of Multipotent Neural Stem Cells and Their Progeny," filed Apr. 5, 2007.

Weiss et al. reexamination U.S. Appl. No. 90/008,367 (reexamination of U.S. Pat. No. 6,294,346) entitled "Use of Multipotent Neural Stem Cells and Their Progeny for the Screening of Drugs and Other Biological Agents," filed Dec. 7, 2006.

Weiss et al. reexamination U.S. Appl. No. 90/008,581 (reexamination of U.S. Pat. No. 6,497,872) entitled "Neural Transplantation Using Proliferated Multipotent Neural Stem Cells and Their Prodigy," filed Apr. 5, 2007.

Weiss et al. reexamination U.S. Appl. No. 90/008,366 (reexamination of U.S. Pat. No. 7,101,709) entitled "Methods of Screening Biological Agents," filed Dec. 7, 2006.

Weiss, S. et al., "Is there a neural stem cell in the mammalian forebrain?" TINS vol. 19, No. 9, 1996, pp. 387-393.

Weissman, I.L., "Translating Stem and Progenitor Cell Biology to the Clinic: Barriers and Opportunities," Science (2000) 287:1442-1446.

Wohl C A, et al., "Retinoic acid enhances neuronal proliferation and astroglial differentiation in cultures of CNS stem cell-derived precursors," J Neurobiol, vol. 37, pp. 281-290, 1998.

Wolswijk et al., "Identification of an adult-specific glial progenitor cell" Development, 105:387-400 (1989).

Xing et al., "Rat nurr1 is prominently expressed in perirhinal cortex, and differentially induced in the hippocampal dentate gyrus by electroconvulsive vs. kindled seizures," Molecular Brain Research, vol. 47, pp. 251-261, 1997.

Xu et al., "The extreme C terminus of progesterone receptor contains a transcriptional repressor domain that functions through a putative corepressor," Proc. Natl. Acad. Sci., vol. 93, pp. 12195-12199, 1996.

Xu, L. et al., "Glucocorticoid receptor and protein/RNA synthesis-dependent mechanisms underlie the control of synaptic plasticity by stress," PNAS, vol. 95, pp. 3204-3208, 1998.

Yamada et al., "NMDA receptor mediated Ca2+ responses in neurons differentiated from p53-/-immortalized Murin neural stem cells," (1999) Neurosci. Letters 264, pp. 165-167.

Yan J. et al., "Differentiation and Tropic/Trophic Effects of Exogenous Neural Precursors in the Adult Spinal Cord," vol. 480, pp. 101-114, 2004.

Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.

Ye et al., "FGF and Shh Signals Control Dopaminergic and Serotonergic Cell Fate in the Anterior Neural Plate," Cell vol. 93:755-766 (1998).

Yoshimoto, Y. et al, "The Effect of Cool Storage on the Survivability of Intraventricular Rat Fetal Ventral Mesencephalic Graft," Duke Med Cent Lib 34.P 1, p. 208, 1991.

Zeller et al., "The Timely Expression of Myelin Basic Protein Gene in Cultured Rat Brain Oligodendrocytes is Independent of Continuous Neuronal Influences," The Journal of Neuroscience 5:11 2955-2962 (1985).

Zetterström et al., "Cellular expression of the immediate early transcription factors Nurr I and NGF1-B suggests a gene regulatory role in several brain regions including the nigrostriatal dopamine system," Molecular Brain Research, vol. 41, pp. 111-120, 1996.

Zetterström et al., "Dopamine Neuron Agenesis in Nurr1-Deficient Mice," Science 276:248-250 (1997).

Zhang, R. et al, "A nitric oxide donor induces neurogenesis and reduces functional deficits after stroke in rats," Ann. Neurol., vol. 50, pp. 602-611, 2001.

Ebert et al.,"Human Neural Progenitor Cells Over-Expressing IGF-1 Protect Dopamine Neurons and Restore Function in a Rat Model of Parkinson's Disease," Experimental Neurology, 209: 213-223 (2008).

HK532

HK532-IGF-I

HK532

HK532-IGF-I

HK532
GAD

HK532-IGF-I
GAD

HK532
VGLUT

HK532-IGF-I
VGLUT

Control

+Aβ

HK532+Aβ

HK532-IGF-I+Aβ

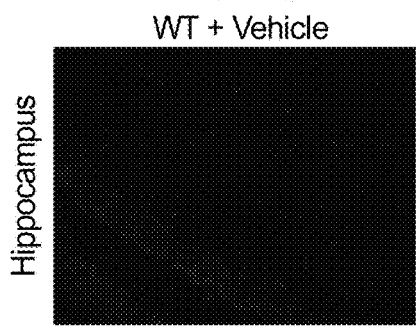
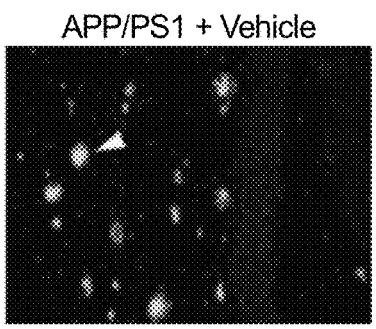
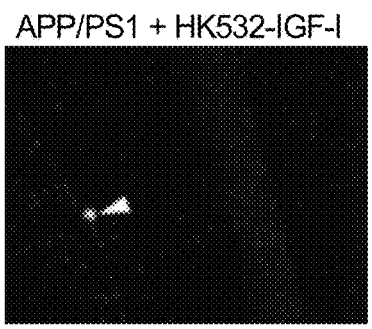
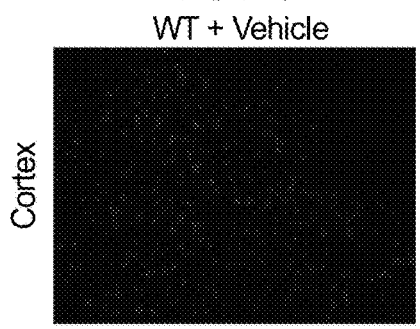
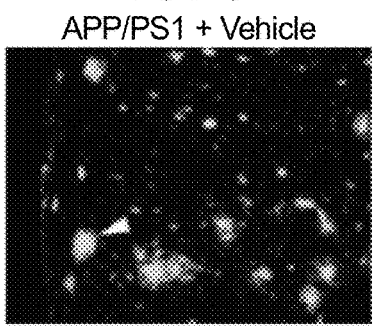
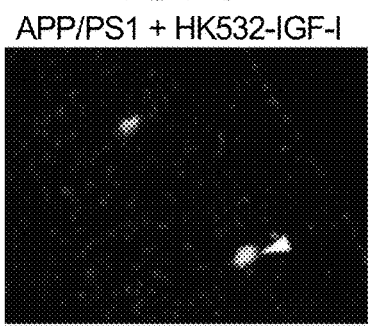
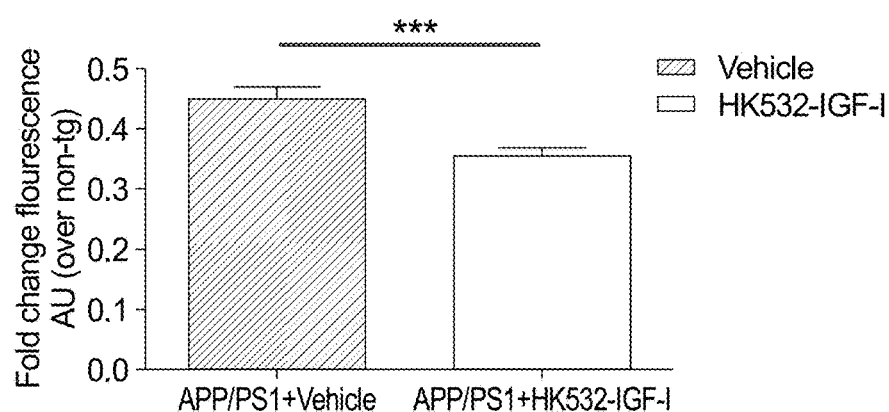
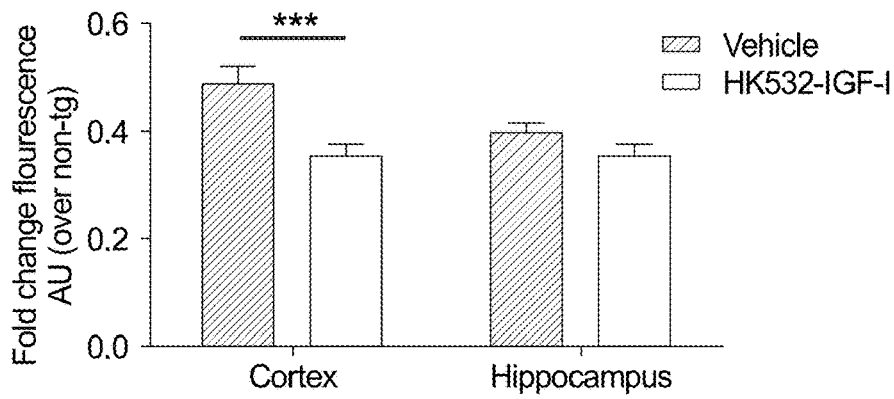

Non-Tg

APP/PS1 + Vehicle

APP/PS1 + HK532-IGF-I

APP/PS1 + HK532-IGF-I

FIG. 9A
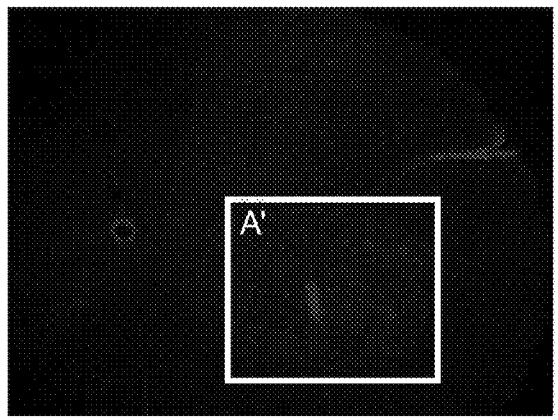
FIG. 9A'
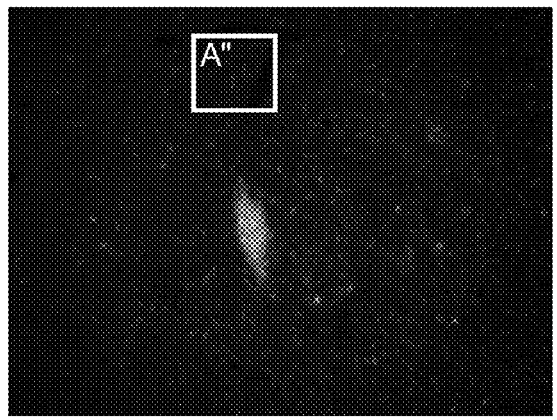
FIG. 9A"
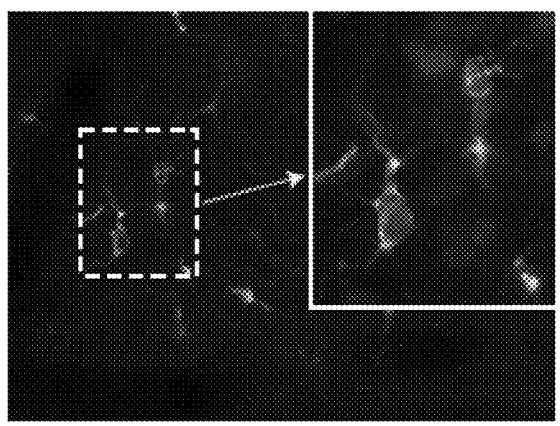
FIG. 9B
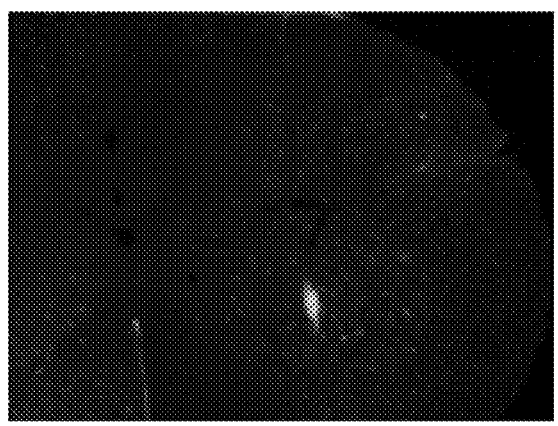
FIG. 9C
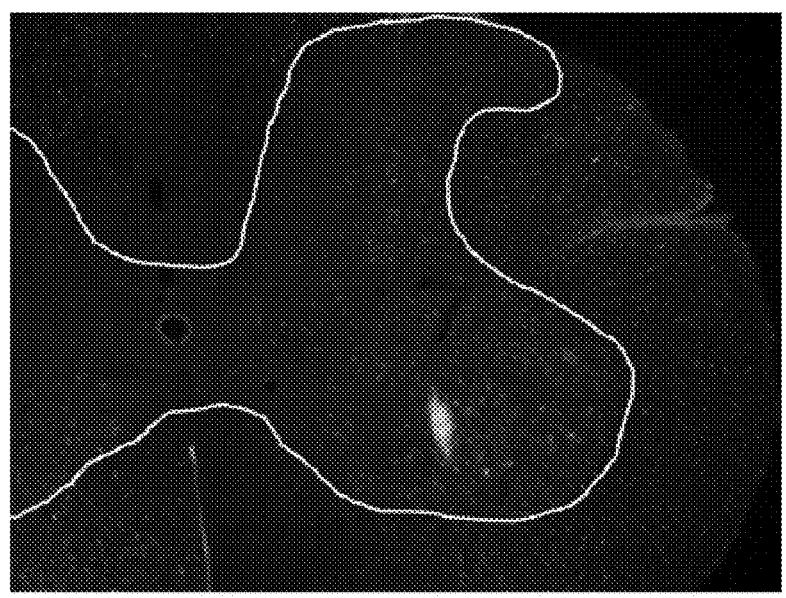

STABLE NEURAL STEM CELLS COMPRISING AN EXOGENOUS POLYNUCLEOTIDE CODING FOR A GROWTH FACTOR AND METHODS OF USE THEREOF

PRIORITY CLAIM

This Application is a continuation of U.S. patent application Ser. No. 14/886,272, filed Oct. 19, 2015, and claims priority to and the benefit of U.S. Provisional Application No. 62/147,950, filed Apr. 15, 2015 and claims priority to and the benefit of U.S. Provisional Application No. 62/066,174, filed Oct. 20, 2014, each of which are incorporated herein by reference.

BACKGROUND

Due to the critical role of insulin-like growth factor-1 (IGF-1) in development and survival of cells in the mammalian central nervous system (CNS), this protein has been considered a potentially important therapeutic agent for various conditions affecting the CNS. Delivery of IGF-1 by some methods, including viral vectors and intrathecal injection, has shown promise for treatment of ALS in animal models. However, subcutaneous administration of mature recombinant IGF-1 to human patients in clinical trials did not demonstrate efficacy in the treatment of ALS. Thus, there exists a need for improved methods of delivering a therapeutically effective amount of IGF-1 to a site of neuronal cell loss.

SUMMARY

The present disclosure generally relates to a human neural stem cell comprising an exogenous polynucleotide coding for a growth factor including, for example, a neurotrophic factor. In an embodiment, the growth factor is stably expressed by the human neural stem cell. Such human neural stem cells may be used for the treatment of a neurodegenerative disease or disorder in a subject in need thereof (e.g., a human subject having a neurodegenerative disease or disorder).

The present disclosure provides a neural stem cell (e.g., a stable human neural stem cell) that comprises an exogenous polynucleotide coding for insulin-like growth factor 1 (IGF-1). The neural stem cells express including, for example, stably overexpress IGF-1. The neural stem cells that comprise an exogenous polynucleotide coding for IGF-1 surprisingly yield a significantly increased number of GAD65-positive GABAergic neurons compared to neural stem cells that do not comprise an exogenous polynucleotide coding for IGF-1.

The present disclosure also provides a neural stem cell (e.g., a stable human neural stem cell) that comprises an exogenous polynucleotide coding for a growth factor. The neural stem cells express including, for example, stably overexpress the growth factor.

In an embodiment of any of the above-mentioned or below-mentioned embodiments, the growth factor is a neurotrophic factor selected from the group consisting of: insulin-like growth factor 1 (IGF-1), glial cell line-derived neurotrophic factor (GDNF), brain-derived neurotrophic factor (BDNF), neurotrophin-3 (NT-3), and vascular endothelial growth factor (VEGF).

In an embodiment of any of the above-mentioned or below-mentioned embodiments, IGF-1 is an IGF-1 isoform such as IGF-1 isoform 4. In a further embodiment of any of the above-mentioned or below-mentioned embodiments, the IGF-1 isoform 4 has a nucleotide sequence as set forth in SEQ ID NO 1.

In an embodiment of any of the above-mentioned or below-mentioned embodiments, the IGF-1 isoform comprises an N-terminal signal peptide, a mature IGF-1 protein, and an E-peptide.

In an embodiment of any of the above-mentioned or below-mentioned embodiments, the human neural stem cell is derived from tissue selected from the group consisting of: cortex, hippocampus, thalamus, midbrain, cerebellum, hindbrain, spinal cord, and dorsal root ganglia.

In an embodiment of any of the above-mentioned or below-mentioned embodiments, the human neural stem cell is obtained from a fetus or an embryo.

In an embodiment of any of the above-mentioned or below-mentioned embodiments, the human neural stem cell is obtained from a fetus having a gestational age of about 5 to about 20 weeks.

In an embodiment of any of the above-mentioned or below-mentioned embodiments, the human neural stem cell is capable of differentiating into neurons and/or glia.

In an embodiment of any of the above-mentioned or below-mentioned embodiments, the human neural stem is capable of engrafting into the brain and/or spinal cord.

In an embodiment of any of the above-mentioned or below-mentioned embodiments, the human neural stem is immortalized.

In an embodiment of any of the above-mentioned or below-mentioned embodiments, the human neural stem cell is immortalized via infection with a retrovirus that carries an immortalizing gene.

In an embodiment of any of the above-mentioned or below-mentioned embodiments, the exogenous polynucleotide coding for the growth factor is operably linked to a ubiquitin C (UbC) promoter (e.g., a ubiquitin C (UbC) promoter having the nucleotide sequence set forth in SEQ ID NO: 3), a human phosphoglycerate kinase 1 promoter, a human synapsin promoter, or a synthetic CAG promoter.

The present disclosure also provides a human neural stem cell comprising an exogenous polynucleotide coding for insulin-like growth factor 1 (IGF-1), wherein IGF-1 comprises a nucleotide sequence as set forth in SEQ ID NO: 1, and wherein the IGF-1 nucleotide sequence is stably expressed.

In an embodiment of any of the above-mentioned or below-mentioned embodiments, the human neural stem cell is immortalized.

In an embodiment of any of the above-mentioned or below-mentioned embodiments, the exogenous polynucleotide coding for IGF-1 is linked to a ubiquitin C (UbC) promoter (e.g., a ubiquitin C (UbC) promoter having the nucleotide sequence set forth in SEQ ID NO: 3), a human phosphoglycerate kinase 1 promoter, a human synapsin promoter, or a synthetic CAG promoter.

The present disclosure also provides a method for the treatment of a neurodegenerative disease or disorder, the method comprising administering to a subject (e.g., a human subject having a neurodegenerative disease or disorder) a therapeutically effective amount of one or more neural stem cells (e.g., stable human neural stem cells) that comprises an exogenous polynucleotide coding for IGF-1.

The present disclosure also provides a method for the treatment of a neurodegenerative disease or disorder, the method comprising administering to a subject (e.g., a human subject having a neurodegenerative disease or disorder) a therapeutically effective amount of one or more neural stem cells (e.g., stable human neural stem cells) that comprise an exogenous polynucleotide coding for a growth factor.

In an embodiment of any of the above-mentioned or below-mentioned embodiments, the growth factor is a neurotrophic factor selected from the group consisting of: insulin-like growth factor 1 (IGF-1), glial cell line-derived neurotrophic factor (GDNF), brain-derived neurotrophic factor (BDNF), neurotrophin-3 (NT-3), and vascular endothelial growth factor (VEGF).

In an embodiment of any of the above-mentioned or below-mentioned embodiments, IGF-1 is an IGF-1 isoform such as IGF-1 isoform 4. In a further embodiment of any of the above-mentioned or below-mentioned embodiments, the IGF-1 isoform 4 has a nucleotide sequence as set forth in SEQ ID NO 1.

In an embodiment of any of the above-mentioned or below-mentioned embodiments, the IGF-1 isoform comprises an N-terminal signal peptide, a mature IGF-1 protein, and an E-peptide.

In an embodiment of any of the above-mentioned or below-mentioned embodiments, the therapeutically effective amount of one or more human neural stem cells are capable of differentiating into neurons and/or glia.

In an embodiment of any of the above-mentioned or below-mentioned embodiments, the therapeutically effective amount of one or more human neural stem cells are capable of engrafting into the brain or spinal cord.

In an embodiment of any of the above-mentioned or below-mentioned embodiments, the exogenous polynucleotide coding for the growth factor is operably linked to a ubiquitin C (UbC) promoter (e.g., a ubiquitin C (UbC) promoter having the nucleotide sequence set forth in SEQ ID NO: 3), a human phosphoglycerate kinase 1 promoter, a human synapsin promoter, or a synthetic CAG promoter.

In an embodiment of any of the above-mentioned or below-mentioned embodiments, the neurodegenerative disease or disorder is amyotrophic lateral sclerosis (ALS), spinal cord injury (SCI), traumatic brain injury (TBI), Alzheimer's disease (AD), dementia, mild cognitive impairment, diabetes, diabetes-related CNS complications, peripheral neuropathy, retinal neuropathy, or multiple sclerosis.

In an embodiment of any of the above-mentioned or below-mentioned embodiments, the spinal cord injury is a traumatic spinal cord injury or an ischemic spinal cord injury.

In an embodiment of any of the above-mentioned or below-mentioned embodiments, the therapeutically effective amount of one or more neural stem cells are injected into an area of neurodegeneration.

In an embodiment of any of the above-mentioned or below-mentioned embodiments, the therapeutically effective amount of one or more neural stem cells are administered to about 5 to about 50 sites in the area of neurodegeneration.

In an embodiment of any of the above-mentioned or below-mentioned embodiments, the one or more sites are separated by a distance of approximately 100 microns to about 5000 microns.

In an embodiment of any of the above-mentioned or below-mentioned embodiments, at least 20%, 30%, 40%, 50%, 60%, 70%, 80%, 90%, 95% or more of the therapeutically effective amount of one or more neural stem cells are capable of generating neurons at the area of neurodegeneration.

In an embodiment of any of the above-mentioned or below-mentioned embodiments, the subject is human.

The present disclosure also provides a method of making cell a human neural stem cell comprising an exogenous polynucleotide coding for a growth factor, wherein the growth factor is stably expressed, the method comprising: obtaining one or more human neural stem cells; plating the one or more neural stem cells on a tissue culture-treated dish precoated with poly D-lysine and fibronectin; culturing the one or more neural stem cells in growth medium (e.g., serum-free growth media); expanding the one or more neural stem cells to produce a population of expanded neural stem cells; and infecting the neural stem cells with a vector that encodes a growth factor. In an embodiment, the expanded neural stem cells are immortalized by infecting the expanded neural stem cells with a retrovirus that encodes an immortalizing gene.

In an embodiment of any of the above-mentioned or below-mentioned embodiments, the growth factor is a neurotrophic factor selected from the group consisting of: insulin-like growth factor 1 (IGF-1), glial cell line-derived neurotrophic factor (GDNF), brain-derived neurotrophic factor (BDNF), neurotrophin-3 (NT-3), and vascular endothelial growth factor (VEGF).

In an embodiment of any of the above-mentioned or below-mentioned embodiments, IGF-1 is an IGF-1 isoform such as IGF-1 isoform 4. In a further embodiment of any of the above-mentioned or below-mentioned embodiments, the IGF-1 isoform 4 has a nucleotide sequence as set forth in SEQ ID NO 1.

In an embodiment of any of the above-mentioned or below-mentioned embodiments, the IGF-1 isoform comprises an N-terminal signal peptide, a mature IGF-1 protein, and an E-peptide.

In an embodiment of any of the above-mentioned or below-mentioned embodiments, the human neural stem cells are obtained from tissue isolated post-mortem from aborted human fetuses.

In an embodiment of any of the above-mentioned or below-mentioned embodiments, the human neural stem cells are infected with a replication-deficient retrovirus bearing a copy of the Myc-ER fusion gene.

The present disclosure provides method of reducing amyloid beta (Aβ) deposition in a subject's brain, clearing Aβ deposits in a subject's brain (e.g. hippocampus and/or cortex), or preventing Aβ accumulation in a subject's brain, the method comprising: administering to one or more areas of the subject's brain a therapeutically effective amount of one or more human neural stem cells comprising an exogenous polynucleotide coding for IGF-1.

The present disclosure provides methods of increasing a number of cholinergic neurons in a subject's brain (e.g., hippocampus and/or cortex), the method comprising: administering to one or more areas of the subject's brain a therapeutically effective amount of one or more human neural stem cells comprising an exogenous polynucleotide coding for IGF-1.

The present disclosure also provides methods of restoring synapses in a subject's brain, the method comprising: administering to one or more areas of the subject's brain a therapeutically effective amount of one or more human neural stem cells comprising an exogenous polynucleotide coding for IGF-1.

The present disclosure provides methods for restoring a subject's memory and/or cognition, the method comprising: administering to one or more areas of a subject's brain a therapeutically effective amount of one or more human neural stem cells comprising an exogenous polynucleotide coding for IGF-1.

BRIEF DESCRIPTION OF THE FIGURES

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 6A-H. Aβ levels are significantly reduced with HK532-IGF-I transplantation. Fluorescence microscopy shows distinct formation of Aβ plaques (arrowheads) in the hippocampus (A-C) and cortex (D-F) of APP/PSI vehicle-treated mice. The plaques were visibly abated with HK532-IGF-I treatment. Nuclei were stained with DAPI (blue) in all sections. Scale Bar: 100 µm. (G) Quantification of fluorescence intensity (A.U.) change from the non-tg of vehicle- and NSC-treated groups shows significantly reduced levels of Aβ in HK532-IGF-I-treated mice compared to sham, suggesting HK532-IGF-I mediates Aβ accumulation. *P<0.001 (H) Comparison of Aβ fluorescence levels specifically in the cortex and hippocampus show significant reduction in Aβ deposition in cortical sections of NSC-injected mice compared to the vehicle-injected mice, *P<0.001, but the decreased levels in the hippocampal sections were not significant.

FIGS. 9A, 9A', 9A", 9B, and 9C. Frozen-immunohistochemistry showing presence of human cell grafts in the ventral horn and a wide distribution throughout the gray- and white-matter In each of FIG. 9A-C SC121 (green) shows all human cytoplasm and DAPI (blue) shows all cell nuclei.

DETAILED DESCRIPTION

Figure 1A:
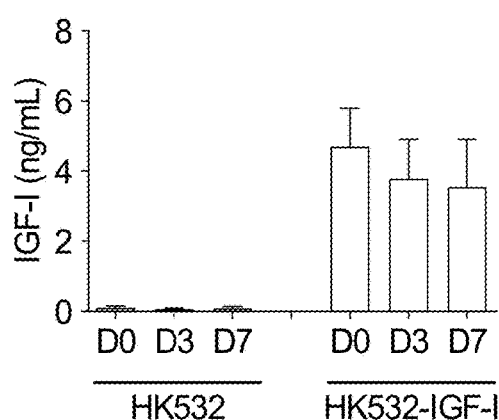
FIG. 1A-C. IGF-I production and signaling in HK532 and HK532-IGF-I cells. (A) Production of IGF-I in HK532 and HK532-IGF-I throughout early differentiation. (B) Representative ICC images of D7 HK532 and HK532-IGF-I labeled with DAPI (blue) and IGF-IR (green). Scale bar 50 µm. (C) Western blot analysis of IGF-I signaling in undifferentiated and differentiated (D7) HK532 and HK532-IGF-I. Cells were treated with an inhibitor panel of LY, U, or NVP for 1 h, followed by IGF-I treatment for 30 min. All blots were probed with pIGF-IR, IGF-IR, pERK, ERK, pAKT and AKT. β-actin was used as a loading control.

The present disclosure provides neural stem cells (e.g., human neural stem cells derived from a fetus or an embryo) that comprise an exogenous polynucleotide coding for a growth factor including, for example, a neurotrophic factor, wherein the growth factor is stably expressed by the neural stem cell. The inventors have discovered that neural stem cells are surprisingly able to engraft at a site of neuronal cell loss and stably express a growth factor including, for example, a neurotrophic factor such as mature IGF-1 in a therapeutically effective amount. Neurotrophic factors may include, for example, insulin-like growth factor 1 (IGF-1) (e.g., an IGF-1 isoform having the sequence set forth in SEQ ID NO: 1), glial cell line-derived neurotrophic factor (GDNF), brain-derived neurotrophic factor (BDNF), neurotrophin-3 (NT-3), or vascular endothelial growth factor (VEGF). However, any protein that can be secreted by a neural stem cell is contemplated for use in the present disclosure. Such human neural stem cells may be obtained from a neural stem cell line and may be used for the treatment of a neurodegenerative disease or disorders including various CNS indications including but not limited to amyotrophic lateral sclerosis (ALS), spinal cord injury (SCI), traumatic brain injury (TBI), Alzheimer's disease (AD), dementia, mild cognitive impairment, diabetes, diabetes-related CNS complications, peripheral neuropathy, retinal neuropathy, and multiple sclerosis.

Surprisingly, the inventors have discovered that human neural stem cells that comprise an exogenous polynucleotide coding for IGF-1, wherein IGF-1 is stably expressed by the neural stem cells, yield (i.e., can differentiate into and/or support the growth of) a significantly increased number of GAD65-positive GABAergic neurons versus neural stem cells that do not comprise the exogenous polynucleotide coding for IGF-1. This is therapeutically relevant to Alzheimer's disease since degeneration specifically of GABAergic neurons has been reported in mouse models and human patients (Loreth et al. (2012) *Neurobiol Dis,* 2012. 47(1): p. 1-12; Schwab et al. (2013) *J Alzheimers Dis,* 2013. 33(4): p. 1073-88). Thus, transplantation of neural stem cells that stably express IGF-1 provide a source of de novo GABAergic neurons to replace those selectively lost in Alzheimer's disease and restore critical neurocircuitry in the brain.

The neural stem cells of the present disclosure that express a growth factor may be stable and multipotent in that they engraft efficiently into the brain and spinal cord, differentiate en masse into neurons and glia, and integrate with the host tissue. Such integration includes the formation of synaptic connections between host neurons and grafted stem cell-derived neurons. An advantage of stable engraftment and integration in the CNS is that the cell graft and thereby production of the growth factor may be constant and stable for as long as the cell is alive. Furthermore, formation of synaptic contact between host neurons and grafted neurons enables direct delivery of growth factor into the synaptic and interstitial spaces adjacent to damaged or diseased neurons. Moreover, the neural stem cells themselves are therapeutic, producing a wide variety of known growth factors and replacing neurons that may be lost to the disease process.

Additionally, the neural stem cells of the disclosure provide an advantage in that their glial progeny migrate widely throughout the brain and spinal cord while their neuronal progeny stay localized in the proximity of a site where they are injected. This property enables one to selectively target either localized delivery of a growth factor via the neurons or widely distributed delivery throughout the CNS via the glia. An advantage of the neuronal secretion of a growth factor such as a neurotrophic factor like IGF-1, GDNF, BDNF, NT3, NGF, VEGF, and others is that even a small amount of the growth factor can reach therapeutic doses since it is continually released into the extracellular space adjacent to target cells, including the limited space of the synaptic cleft immediately adjacent to a high concentration of the corresponding receptor, whereupon it can be internalized by the target cell and transported retrogradely (Rind et al. (2005), *J Neurosci* 25:539-549).

Furthermore, neural stem cells are disclosed that as a result of their origin or their growth conditions can generate a desired proportion of neurons and/or glia (e.g., generate 60% neurons and 40% glia). Those neural stem cells that generate a higher proportion of neurons can be used as needed to deliver a growth factor locally to a specific target region, whereas those that generate a higher proportion of glia can be used to deliver a growth factor more globally. Examples of growth factors that may be desirable to administer locally include, but are not limited to, neurotrophic factors such as IGF-1, NGF, NT3, or BDNF that have pleiotrophic effects. Examples of growth factors that may be desirable to administer globally include, but are not limited to, proteins for enzyme replacement such as for treatment of lysosomal diseases, monoclonal antibodies against cytokines, cytokine receptors, or growth factor receptors.

Figure 1B:
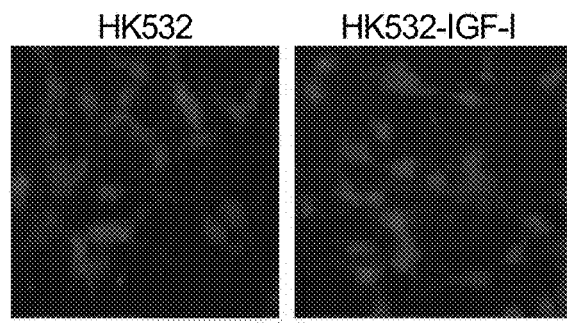
Figure 1C:
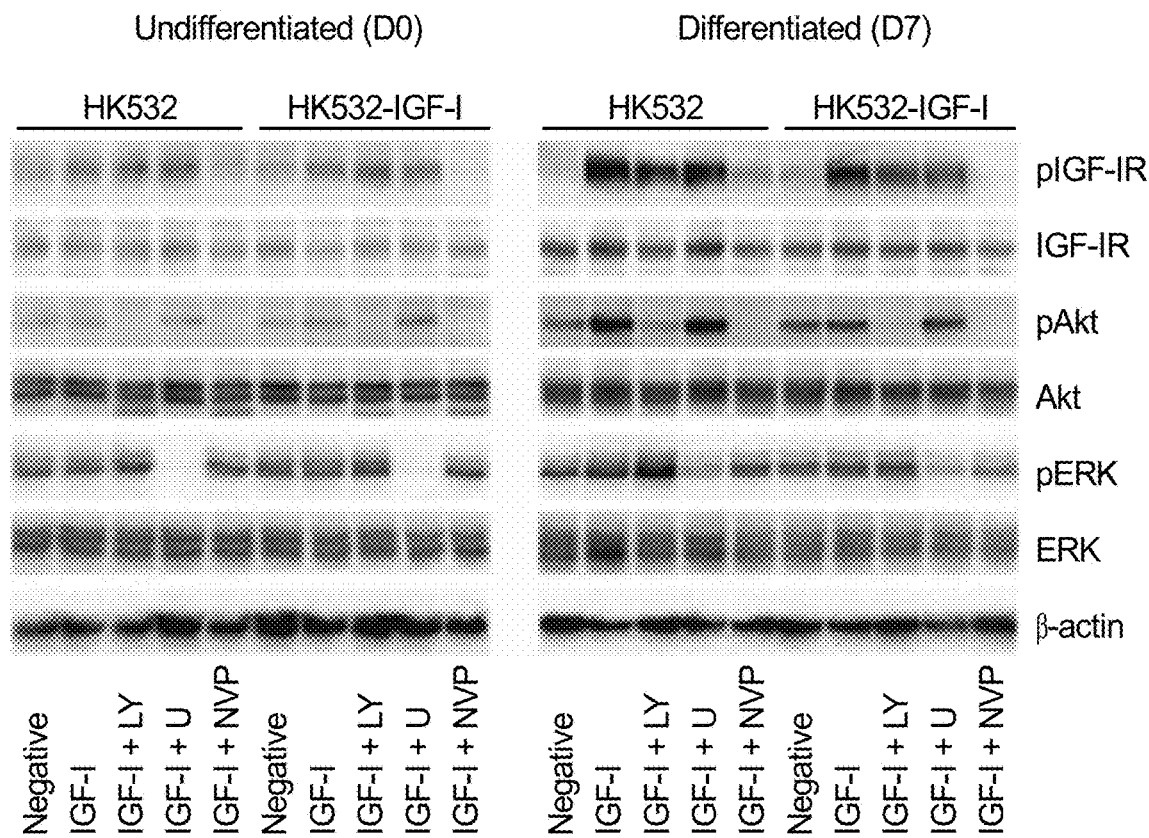
Figure 2A:
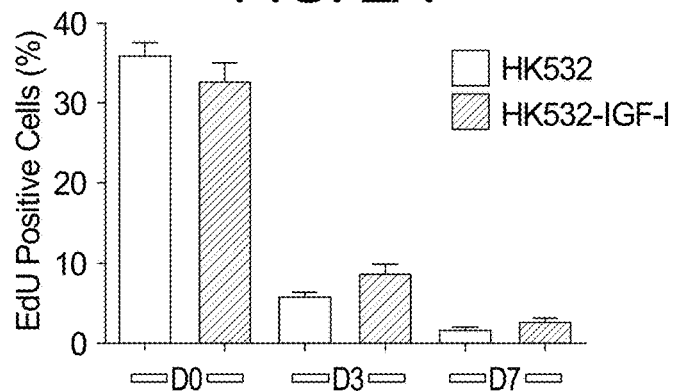
FIG. 2A-G. Induced IGF-I expression does not affect HK532 proliferation and migration. (A) Quantification of the percent of EdU-positive cells at D0, D3, and D7 in HK532 and HK532-IGF-I cultures. (B-E) Representative ICC images of D0 and D7 HK532 and HK532-IGF-I labeled with DAPI (blue) and EdU (green). Scale bar 200 µm. (F-G) Quantification of absorbance of migrated HK532 and HK532-IGF-I at D0 and D7.
Figure 2B:
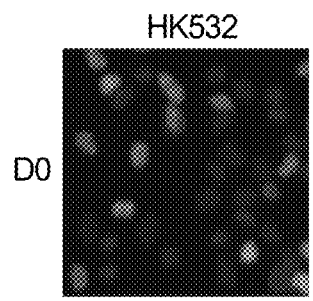
Figure 2C:
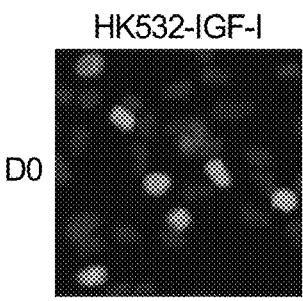
Figure 2D:
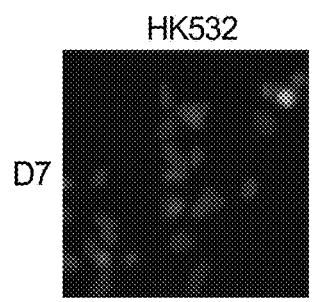
Figure 2E:
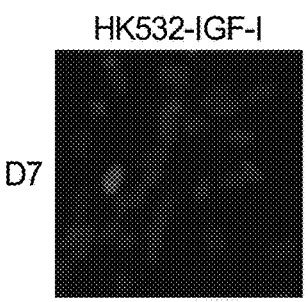
Figure 2F:
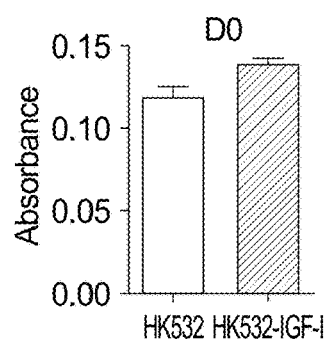
Figure 2G:
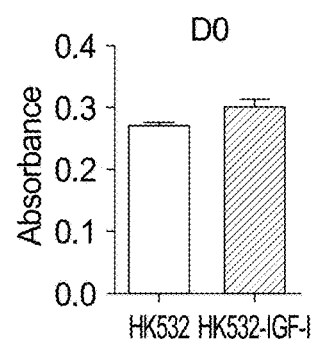
Figure 3A:
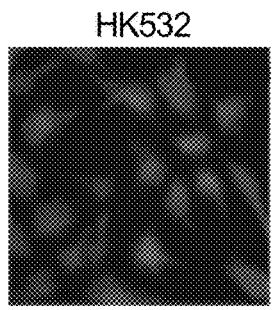
FIG. 3A-F. Induced IGF-I expression does not affect maintenance of progenitor status or neurite outgrowth during differentiation. (A-B) Representative ICC image of D0 HK532 and HK532-IGF-I labeled with DAPI (blue) and Nestin (red). (C) Quantification of Nestin-positive D0 HK532 and HK532-IGF-I. (D-E) Representative ICC image of D7 HK532 and HK532-IGF-I labeled with DAPI (blue) and TUJ1 (red). (F) Quantification of the neural index measurement ($µm^2$/cell). Scale bar 200 µm.
Figure 3B:
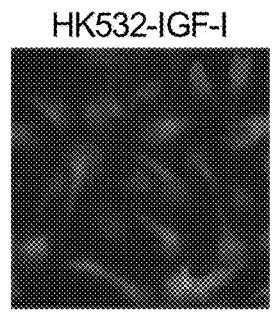
Figure 3C:
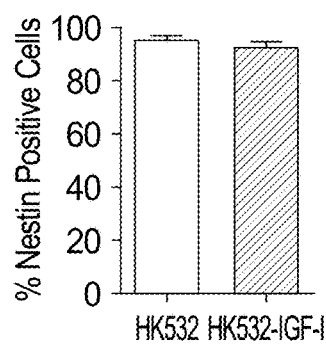
Figure 3D:
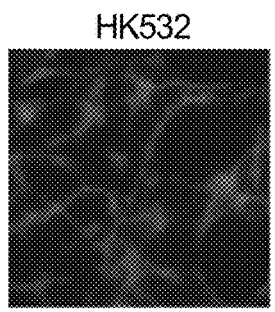
Figure 3E:
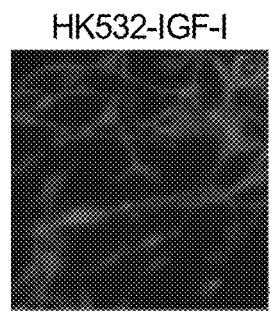
Figure 3F:
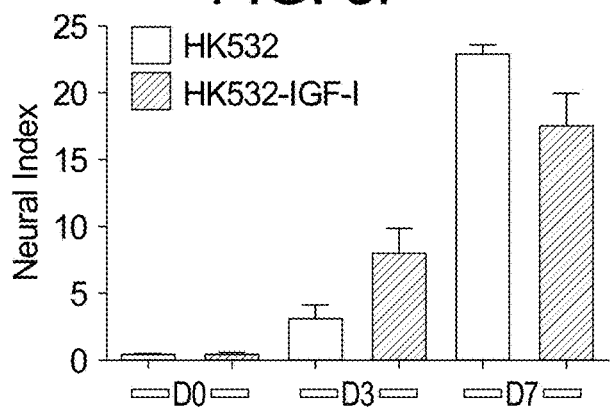
Figure 4A:
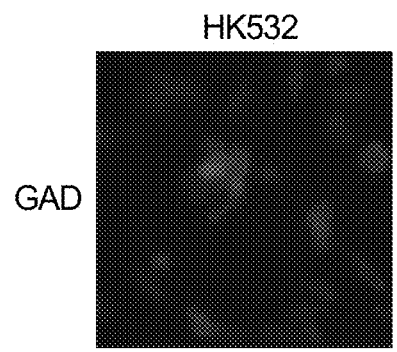
FIG. 4A-F. Terminal phenotype of HK532 and HK532-IGF-I cells. (A-B) Representative ICC images of D7 HK532 and HK532-IGF-I cells labeled with DAPI (blue) and GAD65 (green). (C-D) Representative ICC image of D7 cells labeled with DAPI (blue) and VGLUT (red). Scale bar 200 µm. (E) Quantification of GAD65-positive GABAergic neurons in HK532 and HK532-IGF-I cells. HK532-IGF-I cells preferentially differentiate into GABAergic neurons (*p<0.05). (F) Quantification of VGLUT-positive glutamatergic neurons in HK532 and HK532-IGF-I cells.
Figure 4B:
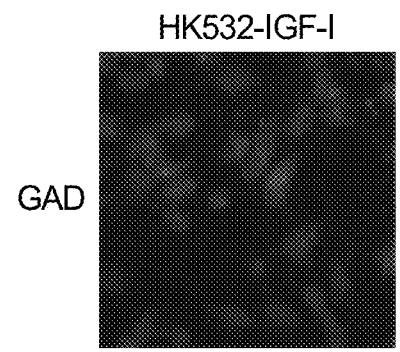
Figure 4C:
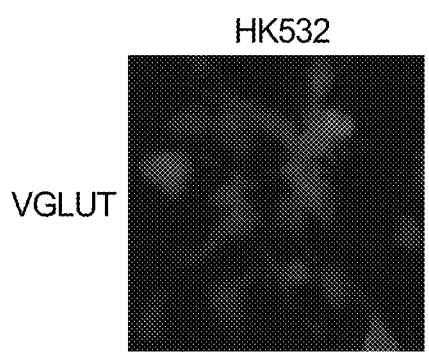
Figure 4D:
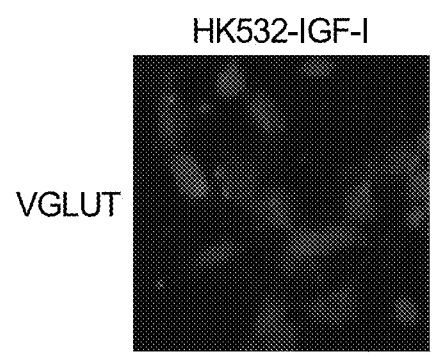
Figure 4E:
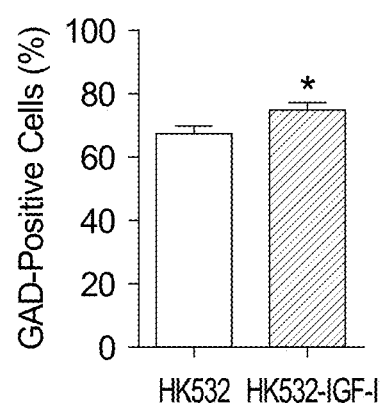
Figure 4F:
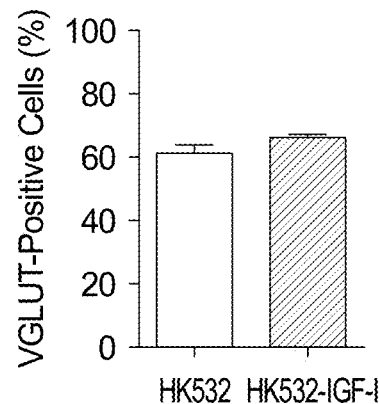
Figure 5A:
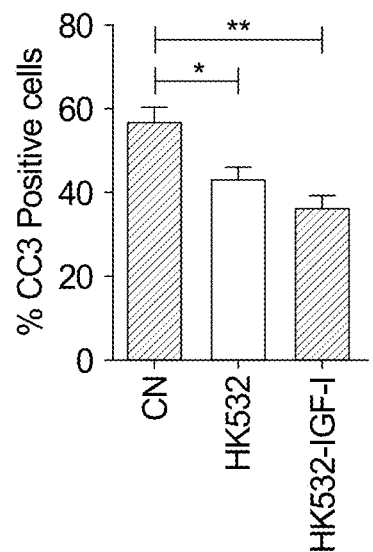
FIG. 5A-H. HK532-IGF-I cells are neuroprotective and survive grafting into APP/PS1 AD and WT mice. (A) Quantification of apoptosis and CC3 activation in response to Aβ toxicity in primary CN, HK532 and HK532-IGF-I. Both HK532 cell lines are more resistant than CN (*p<0.05). (B-D) Representative ICC images of primary CN labeled with DAPI and CC3 (scale bar 200 µm). (B) Control CN with no Aβ treatment, (C) CN with Aβ treatment, (D) CN with Aβ treatment co-cultured with HK532 and (E) CN with Aβ treatment co-cultured with HK532-IGF-I. (F) Quantification of Aβ-mediated apoptosis and CC3 activation in CN/HK532 co-cultures. HK532-IGF-I exhibited an increased neuroprotective capacity compared to HK532 (*p<0.05). (G-H) Representative images of DAPI, HuNu and DCX labeling of human early neural precursors in the hippocampal area of (G) APP/PS1 AD animals and (H) WT animals 10 weeks following transplantation into the fimbria fornix (10× scale bar 200 µm; 60× scale bar 50 µm).
Figure 5B:
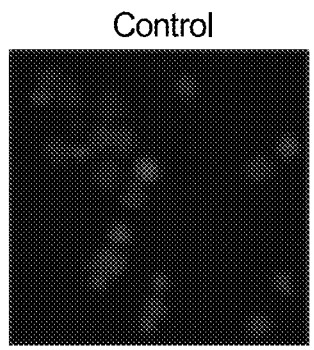
Figure 5C:
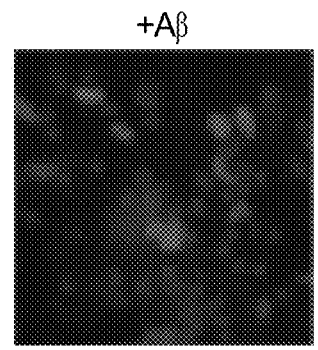
Figure 5D:
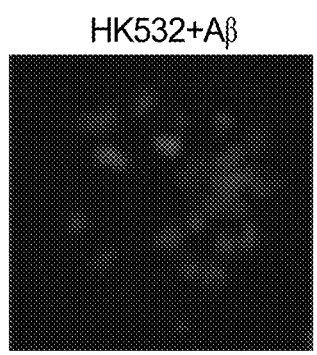
Figure 5E:
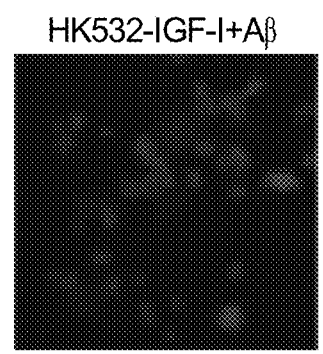
Figure 5F:
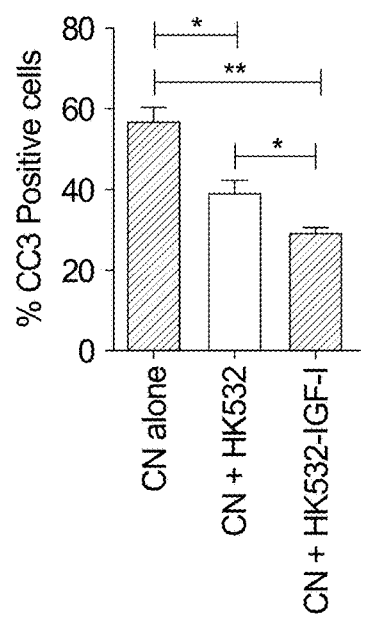
Figure 5G:
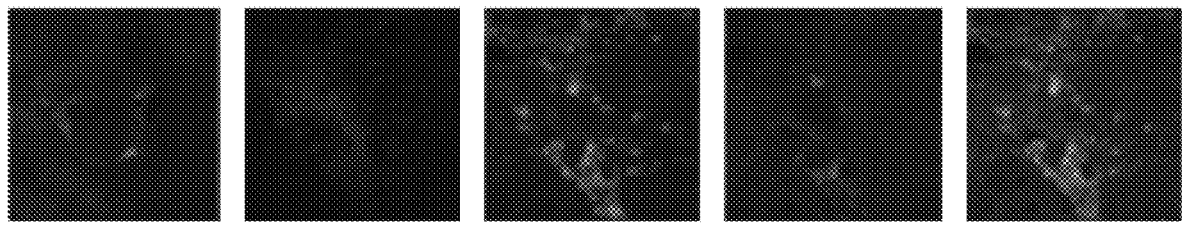
Figure 5H:
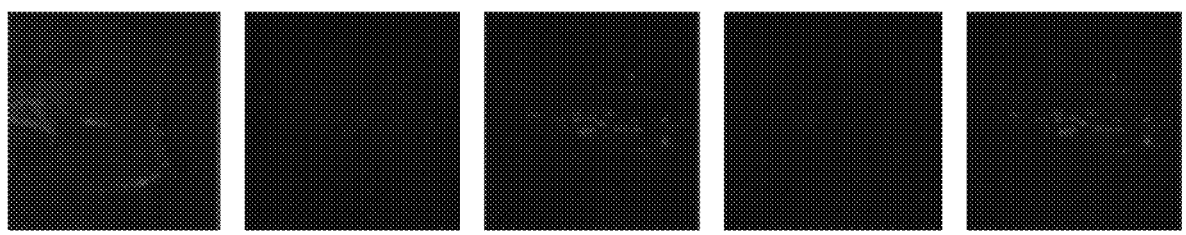

In an embodiment, the growth factor is a neurotrophic factor such as IGF-1 including, for example, an IFG1 isoform at set forth in FIG. 1. The IGF-1 isoform may be IGF-1 isoform 4. In an embodiment, the IGF-1 isoform 4 has a nucleotide sequence as set forth in SEQ ID NO 1 (amino acid sequence set forth in SEQ ID NO: 2). This isoform contains three different potential biological effectors: the mature IGF-1 protein capable of binding various IGF binding proteins as well as the IGF-1 receptor; the carboxy (C—) terminal MGF peptide released during pro-IGF-1 processing which may act as neuroprotectant against ischemia and other deleterious conditions via mechanisms independent of IGF-1 receptor; and the amino (N—) terminal signal peptide released during pre-pro-IGF-1 processing.

IGF-1 biology is complex. Six different forms of human IGF-1 mRNA transcripts are produced under the control of two different promoters (reviewed in Barton (2006), *J Appl Physiol* 100:1778-1784), all of which produce a single mature IGF-1 protein. The various transcripts are translated to the mature IGF-1 protein during which time distinct cleavage products are produced. The transcript isoforms and the various cleavage products are known to be tissue specific. Thus, although 75% of the circulating mature IGF-1 protein is produced by liver, several other tissues including muscle, kidney, and brain/spinal cord produce their own IGF-1 transcripts and protein. Also, IGF-1 levels in the brain for instance are regulated independently of plasma level of IGF-1 (Adams et al. (2009), *Growth Factors* 27:181-188). Notably, rat and mouse IGF-1 genes are regulated differently than the human IGF-1 gene to result in non-equivalent IGF-1 isoforms between the species (Barton (2006), *Appl. Physiol. Nutr. Metab.* 31:791-797).

A dose (e.g., a therapeutically effective dose) and localization of a growth factor in the CNS may be varied by using different promoters and also by using different neural stem cell lines with distinct differentiation and migratory properties. For example, the synapsin promoter can be used to drive expression at low-to-moderate levels primarily in neuronal progeny, therefore ensuring localized distribution to target neuronal populations. In contrast, a Ubiquitin C promoter can be used to direct expression to both neuronal and glial cell progeny, enabling broader distribution of the growth factor. Additionally, the synthetic CAG promoter, which consists of the cytomegalovirus (CMV) enhancer fused to the chicken β-actin promoter, can direct very high levels of expression of the growth factor. Further, neural stem cells that generate a higher proportion of neurons can be used as needed to deliver a growth factor locally to a specific target region, whereas those neural stem cells that generate a higher proportion of glia can be used to deliver the growth factor more globally. Examples of growth factors that may be desirable to administer locally include, but are not limited to, neurotrophic factors such as IGF-1, NGF, NT3, or BDNF that have pleiotrophic effects. Examples of growth factors that may be desirable to administer globally include, but are not limited to, proteins for enzyme replacement such as for treatment of lysosomal diseases, monoclonal antibodies against cytokines, cytokine receptors, or growth factor receptors.

Neural Stem Cells

Neural stem cells (e.g., stable human neural stem cells) are provided that comprise an exogenous polynucleotide coding for a growth factor such as a neurotrophic factor. The neurotrophic factor may be insulin-like growth factor 1 (IGF-1), glial cell line-derived neurotrophic factor (GDNF), brain-derived neurotrophic factor (BDNF), neurotrophin-3 (NT-3), or vascular endothelial growth factor (VEGF). Also provided are neural stem cell lines that comprise neural stem cells having an exogenous polynucleotide coding for a growth factor. The neural stem cells are preferably stable and do not differentiate in culture even after more than sixty cell doublings.

The present disclosure provides a neural stem cell (e.g., a stable human neural stem cell) that comprises an exogenous polynucleotide coding for insulin-like growth factor 1 (IGF-1). The neural stem cells express including, for example, stably overexpress IGF-1. The neural stem cells that comprise an exogenous polynucleotide coding for IGF-1 surprisingly yield a significantly increased number of GAD65-positive GABAergic neurons compared to neural stem cells that do not comprise an exogenous polynucleotide coding for IGF-1. The neural stem cells are preferably stable and do not differentiate in culture even after more than sixty cell doublings.

The present disclosure provides a stable human neural stem cell that expresses an exogenous polynucleotide coding for insulin-like growth factor 1 (IGF-1).

In an embodiment, the neurotrophic factor is IGF-1 including, for example, an IGF-1 isoform such as IGF-1 isoform 4 having the sequence set forth in SEQ ID NO: 1. Surprisingly, the inventors have discovered that IGF-1 isoform 4 having the sequence set forth in SEQ ID NO: 1 is functional when expressed by the neural stem cells (e.g., it binds its receptor an initiates a signal transduction process that has a physiological impact). Such a finding was entirely unexpected as some prior reports indicated that the administration of neural stem cells that express mature IGF-1 was ineffective in providing a functional benefit (i.e., the neural stem cells were ineffective in treating a disease or disorder).

As used herein, the term, "neural stem cell" or "NSC" refers to a multipotential stem cell that can be functionally defined according to their capacity to differentiate into each of the three major cell types of the central nervous system (CNS): neurons, astrocytes, and oligodendrocytes. As used herein, the term "stem cell" refers to an undifferentiated cell that is capable of self-renewal, meaning that with each cell division at least one daughter cell will also be a stem cell. NSCs can also refer to neural or neuronal progenitors, or neuroepithelial precursors.

The present disclosure also provides methods of making cell a human neural stem cell comprising an exogenous polynucleotide coding for a growth factor, wherein the growth factor is stably expressed, the method comprising: obtaining one or more human neural stem cells; plating the one or more neural stem cells on a tissue culture-treated dish precoated with poly D-lysine and fibronectin; culturing the one or more neural stem cells in serum-free growth medium; expanding the one or more neural stem cells to produce a population of expanded neural stem cells; infecting the expanded neural stem cells with a retrovirus that encodes an immortalizing gene; and infecting the neural stem cells previously infected with a retrovirus with a vector that encodes a growth factor. Such immortalized neural stem cells and methods of making the neural stem cells are disclosed in U.S. Pat. No. 7,544,511.

In one embodiment, the NSCs are multipotent such that each cell has the capacity to differentiate into a neuron, astrocyte or oligodendrocyte. In another embodiment, the NSCs are bipotent such that each cell has the capacity to differentiate into two of the three cell types of the CNS. In another embodiment, the NSCs include at least bipotent cells generating both neurons and astrocytes in vitro and include at least unipotent cells generating neurons in vivo.

Growth conditions can influence the differentiation direction of the cells toward one cell type or another, indicating that the cells are not committed toward a single lineage. In culture conditions that favor neuronal differentiation, cells, particularly from human CNS, are largely bipotent for neurons and astrocytes and differentiation into oligodendrocytes is minimal. Thus, the differentiated cell cultures of the disclosed methods may give rise to neurons and astrocytes.

In an embodiment, the NSCs are isolated from the CNS. As used herein, the term "isolated" with reference to a cell, refers to a cell that is in an environment different from that which the cell naturally occurs (e.g. where the cell naturally occurs in an organism) and the cell is removed from its natural environment.

NSCs may be isolated from an area which is naturally neurogenic for a desired population of neurons and from embryonic, fetal, post-natal, juvenile or adult tissue. The desired population of cells may include the cells of a specific neuronal phenotype which can replace or supplement such phenotype lost or inactive in the course of disease progression. In an embodiment, the NSCs are isolated from the subventricular zone (SVZ) or from the subgranular zone of the dentate gyrus (DG). In preferred embodiments, the NSCs are isolated from the spinal cord in which neurogenesis of ventral motor-neurons is substantial and obtained at a gestational age of human fetal development during which neurogenesis of ventral motor-neurons is substantial.

Accordingly, in an embodiment, NSCs are isolated from the spinal cord at a gestational age of about 6.5 to about 20 weeks. Preferably, NSCs are isolated from the spinal cord at a gestational age of about 7 to about 9 weeks. In another embodiment the NSCs are isolated from embryonic spinal cord tissue. In yet another embodiment, neural stem cells are isolated from a human. It should be appreciated that the proportion of the isolatable NSC population can vary with the age of the donor. Expansion capacity of the cell populations can also vary with the age of the donor.

The NSCs of the ventral midbrain, for example, are distinct from the NSCs obtained from the spinal cord at the same gestational stage. In particular, the NSCs from the ventral midbrain can give rise to tyrosine-hydroxylase-expressing dopaminergic neurons, whereas NSCs from the spinal cord can generate acetylcholine-producing cholinergic neurons. Both cell types, however, simultaneously generate the more ubiquitous glutamate- and GABA-producing neurons. Therefore, in an embodiment, the disclosed methods include obtaining NSCs from the spinal cord to treat conditions ameliorated or attenuated, at least in part, by the implantation of acetylcholine-producing cholinergic neurons.

NSCs can also be isolated from post-natal and adult tissues. NSCs derived from post-natal and adult tissues are quantitatively equivalent with respect to their capacity to differentiate into neurons and glia, as well as in their growth and differentiation characteristics. However, the efficiency of in vitro isolation of NSCs from various post-natal and adult CNS can be much lower than isolation of NSCs from fetal tissues which harbor a more abundant population of NSCs. Nevertheless, as with fetal-derived NSCs, the disclosed methods enable at least about 30% of NSCs derived from neonatal and adult sources to differentiate into neurons in vitro. Thus, post-natal and adult tissues can be used as described above in the case of fetal-derived NSCs.

In an embodiment, human fetal spinal tissue is dissected under a microscope. A region of tissue corresponding to the lower cervical/upper thoracic segments is isolated. The NSCs are isolated, pooled, and expanded on poly-D-lysine coated culture vessels in a media containing fibronectin and basic fibroblast growth factor (bFGF; FGF-2). Cells are expanded and then concentrated to the desired target cell density of about 10,000 cells per microliter in a medium free of preservative and antibiotics. Concentrated cells may be used fresh for implantation or frozen for later use.

In an embodiment, the NSCs are derived from embryonic stem cells or induced pluripotent stem cells. As used herein, the term "embryonic stem cell," refers to a stem cell isolated from the developing embryo which can give rise to all of the cells of the body (e.g., cells of the ecto-, meso-, and/or endo-dermal cell lineages). The term "induced pluripotent stem cell," as used herein, refers to a stem cell derived from a somatic cell (e.g., a differentiated somatic cell) that has a higher potency than the somatic cell. Embryonic stem cells and induced pluripotent stem cells are capable of differentiation into more mature cells (e.g., neural stem cells or neural progenitor cells). Methods employed for growing and differentiating embryonic or induced pluripotent stem cells into NSCs in vitro can, for example, be such as those described in Daadi et al., *PLoS One.* 3(2):e1644 (2008).

There are several standard molecular biology techniques that may be used to regulate expression of a polynucleotide encoding a growth factor in a neural stem cell as disclosed herein. For example, different promoters may be used to regulate the level of expression of the growth factor and/or regulate which progeny of the neural stem cell will express the factor. For example, a human Ubiquitin C (UbC), PGK, or CAG promoter confer distinct levels of expression of the growth factor in the differentiated neuronal and glial progeny of the human neural stem cells disclosed herein. A PGK promoter enables production of low levels of growth factor, approximately 0.5 ng protein per million cells per 24 hours, a UbC promoter enables higher amounts of growth factor production, approximately 2 ng protein per million cells per 24 hours, and a CAG promoter enables still higher amounts of growth factor production, approximately 14 ng protein per million cells per 24 hours. Additionally or alternatively, expression may be driven and confined to certain progeny of the neural stem cells. For example, a human synapsin promoter may be used to direct expression of a growth factor to the neuronal progeny of the neural stem cells.

Methods of Treating

Neural stem cells as disclosed herein may be used for in methods for treating diseases or disorders including neurodegenerative diseases or disorders such as amyotrophic lateral sclerosis (ALS), spinal cord injury (SCI), traumatic brain injury (TBI), Alzheimer's disease (AD), dementia, mild cognitive impairment, diabetes, diabetes-related CNS complications, peripheral neuropathy, retinal neuropathy, or multiple sclerosis. Such methods may include administering a therapeutically effective amount of neural stem cells disclosed herein to a subject including, for example, by injection. In an embodiment, a subject treated with the disclosed neural stem cells is immunosuppressed prior to, during, and/or after administration of the neural stem cells.

In some embodiments, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. A neurodegenerative disease or disorder may be considered treated if the subject administered the disclosed neural stem cells exhibits an improvement in a hippocampal-dependent behavioral task as compared to a subject not treated with the disclosed neural stem cells.

The terms "prevention", "prevent", "preventing", "suppression", "suppress", "suppressing", "inhibit" and "inhibition" as used herein refer to a course of action (such as administering a NSC as disclosed herein) initiated in a manner (e.g., prior to the onset of a clinical symptom of a disease state or condition such as deposits of $A\beta$ so as to prevent, suppress or reduce, either temporarily or permanently, the onset of a clinical manifestation of the disease state or condition (e.g., the formation of deposits of $A\beta$. Such preventing, suppressing or reducing need not be absolute to be useful.

In some embodiments, "effective amount," as used herein, refers to the amount of spinal cord-derived neural stem cells that is required to confer a therapeutic effect on the subject. A "therapeutically effective amount," as used herein, refers to a sufficient amount spinal cord-derived neural stem cells being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the spinal cord-derived neural stem cells required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of spinal cord-derived neural stem cells is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician.

The neural stem cells may be transplanted into the motor cortex and/or spinal cord gray matter to rescue degenerative upper and low motor neurons in ALS, transplanted into the site of infarction in acute and chronic stages of ischemic or hemorrhagic stroke to rescue the affected neurons and to reduce the size of penumbra, transplanted into the nucleus basalis of Meynert to protect cholinergic neurons in dementia and Alzheimer's disease patients, transplanted into the hippocampus or other regions of the brain to slow progression of dementia during senility or in Alzheimer's disease or to reduce seizures in epilepsy, transplanted into white matter tracts such as internal capsule and corpus callosum for neuroprotection in traumatic brain injury or in stroke. The neural stem cells from these locations can migrate radially throughout the brain to distribute IGF-1 protein for treatment of other indications such as diabetes and diabetes-related CNS complications. The neural stem cells can be transplanted into the intercostal muscles and/or the diaphragm muscles to increase the muscle endplates and enhance respiratory capacity of ALS or cervical spinal cord injury patients. The neural stem cells can be transplanted into skeletal muscles to increase the muscle fibers in muscular dystrophy and various motor neuron diseases. The neural stem cells can be transplanted into cerebellum and/or brainstem to rescue the motor neurons affected by conditions including spinal muscular atrophy, bulbar muscular atrophy, and cerebellar ataxia. The neural stem cells can be transplanted intraspinally for regeneration of myelinating oligodendrocytes in multiple sclerosis. The neural stem cells can be transplanted into the intrathecal space or into the subarachnoid space for global distribution of the IGF-1 for neuroprotection in enzyme deficiency diseases.

The present disclosure provides methods of reducing amyloid beta (Aβ) deposition (e.g., levels of Aβ deposition) in a subject's brain (e.g. hippocampus and/or cortex), the method comprising: administering to one or more areas of the subject's brain a therapeutically effective amount of one or more human neural stem cells comprising an exogenous polynucleotide coding for IGF-1. The levels of Aβ in the subject's brain may be reduced by 5%, 10%, 15%, 20%, 25%, 30%, 40%, 50%, 60%, 70%, 80%, 90%, 100%, 150%, 200% or greater, including as compared to a subject's brain that is not administered a therapeutically effective amount of one or more human neural stem cells comprising an exogenous polynucleotide coding for IGF-1. The levels of Aβ in the subject's brain may be reduced by 2-fold, 3-fold, 4-fold, 5-fold, 6-fold, 7-fold, 8-fold, 9-fold, 10-fold or greater, including as compared to a subject's brain that is not administered a therapeutically effective amount of one or more human neural stem cells comprising an exogenous polynucleotide coding for IGF-1. In some embodiments, the subject has Alzheimer's disease.

The present disclosure provides methods of clearing Aβ deposits in a subject's brain (e.g. hippocampus and/or cortex), or preventing Aβ accumulation in a subject's brain (e.g. hippocampus and/or cortex), the method comprising: administering to one or more areas of the subject's brain a therapeutically effective amount of one or more human neural stem cells comprising an exogenous polynucleotide coding for IGF-1. In some embodiments, the subject has Alzheimer's disease.

The present disclosure provides methods of preventing Aβ accumulation in a subject's brain (e.g. hippocampus and/or cortex), the method comprising: administering to one or more areas of the subject's brain a therapeutically effective amount of one or more human neural stem cells comprising an exogenous polynucleotide coding for IGF-1. In some embodiments, the subject has Alzheimer's disease.

The present disclosure provides methods of increasing a number of cholinergic neurons in a subject's brain (e.g., hippocampus and/or cortex), the method comprising: administering to one or more areas of the subject's brain a therapeutically effective amount of one or more human neural stem cells comprising an exogenous polynucleotide coding for IGF-1. The number of cholinergic neurons in the subject's brain may be increased by 5%, 10%, 15%, 20%, 25%, 30%, 40%, 50%, 60%, 70%, 80%, 90%, 100%, 150%, 200% or greater, including as compared to a subject's brain that is not administered a therapeutically effective amount of one or more human neural stem cells comprising an exogenous polynucleotide coding for IGF-1. The number of cholinergic neurons in the subject's brain may be increased 2-fold, 3-fold, 4-fold, 5-fold, 6-fold, 7-fold, 8-fold, 9-fold, 10-fold or greater, including as compared to a subject's brain that is not administered a therapeutically effective amount of one or more human neural stem cells comprising an exogenous polynucleotide coding for IGF-1. In some embodiments, the subject has Alzheimer's disease.

The present disclosure also provides methods of restoring synapses in a subject's brain, the method comprising: administering to one or more areas of the subject's brain a therapeutically effective amount of one or more human neural stem cells comprising an exogenous polynucleotide coding for IGF-1. In some embodiments, the subject has Alzheimer's disease.

The present disclosure provides methods for restoring a subject's memory and/or cognition, the method comprising: administering to one or more areas of a subject's brain a therapeutically effective amount of one or more human neural stem cells comprising an exogenous polynucleotide coding for IGF-1. In some embodiments, the subject has Alzheimer's disease.

In an embodiment, the NSCs can be diluted with an acceptable pharmaceutical carrier. The term "pharmaceutically acceptable carrier" as used herein refers to a diluent, adjuvant, excipient, or vehicle with which the cells of the disclosure are administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the neural stem cells and pharmaceutically acceptable carriers can be sterile. Water is a useful carrier when the cells are administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use. The selection of a suitable carrier is within the skill of the ordinary artisan.

Various neuronal subtypes can be obtained from manipulation of neural stem cells expanded in culture. Thus, specific neuronal subtypes, based on the disclosed methods, can be isolated and purified from other irrelevant or unwanted cells to improve the result, as needed, and can be used for treatment of cognitive dysfunction.

The NSCs in the disclosed methods can be derived from one site and transplanted to another site within the same subject as an autograft. Furthermore, the NSCs in the disclosed methods can be derived from a genetically identical donor and transplanted as an isograft. Still further, the NSCs in the disclosed methods can be derived from a genetically non-identical member of the same species and transplanted as an allograft. Alternatively, NSCs can be derived from non-human origin and transplanted as a xenograft. With the development of powerful immunosuppressants, allograft and xenograft of non-human neural precursors, such as neural precursors of porcine origin, can be grafted into human subjects.

A sample tissue can be dissociated by any standard method. In one embodiment, tissue is dissociated by gentle mechanical trituration using a pipette and a divalent cation-free buffer (e.g. saline) to form a suspension of dissociated cells. Sufficient dissociation to obtain largely single cells is desired to avoid excessive local cell density.

For successful commercial application of NSCs, maintaining robust and consistent cultures that have stable expansion and differentiation capacities through many successive passages is desirable. As described above, the culture methods can be optimized to achieve long-term, stable expansion of an individual cell line of NSCs from different areas and ages of CNS development while maintaining their distinct progenitor properties. In one embodiment, stem cells can be cultured according to the methods set forth in U.S. Pat. Nos. 8,460,651, 8,236,299, 7,691,629, 5,753,506, 6,040,180, or 7,544,511, the entireties of which are incorporated by reference herein.

In an embodiment, the NSCs of the disclosed methods can include pre-differentiated cells for transplantation. For maximum yield of the cells and for simplicity of the procedure, a confluent culture is harvested for transplantation which comprises primarily a population of undifferentiated cells. It should be appreciated, however, that a minor population of cells just starting to differentiate spontaneously can also exist due to the increased cell density.

In an embodiment, the NSCs are concentrated in a solution such as the clinically usable, hibernation or freezing solutions described above. In an embodiment, the NSCs are concentrated to an appropriate cell density which can be the same or different from the cell density for administration of the cells. In an embodiment, the cell density for administration can vary from about 1,000 cells per microliter to about 1,000,000 cells per microliter depending upon factors such as the site of the injection, the minimum dose necessary for a beneficial effect, and toxicity side-effect considerations.

Low cell survival of donor cells using known methods has necessitated the delivery of a large quantity of cells to a relatively small area in order to attempt effective treatment. Injection volume, however, is hydrostatic pressure exerted on the host tissue and the prolonged injection time associated with high injection volumes exacerbates surgical risk. Additionally, over-injection of donor cells leads to compression and subsequent injury of the host parenchymal tissue. In attempting to compensate for volume constraints, known methods have required preparation of high cell density suspensions for the injections. However, a high cell density promotes tight clustering of the transplanted cells and inhibits cell migration or spreading preventing effective treatment beyond a limited area and compromising seamless integration into the host tissue.

In contrast, as a result of improved survival in vivo of the cells prepared by the disclosed methods, fewer number of cells are needed per injection. In fact, up to three to four times the number of injected cells have been shown to exist after six months from the time of injection demonstrating significant quantitative survival using the disclosed methods. Also, because of the quantitative survival, reproducible administration of desired cell doses can be achieved. Accordingly, in one embodiment, the NSCs are concentrated to a density of about 1,000 to about 1,000,000 cells per microliter. In one embodiment, the NSCs are concentrated to a density of about 2,000 to about 80,000 NSCs per microliter. In another embodiment, about 5,000 to about 50,000 NSCs per microliter have been used for effective engraftment. In another embodiment, about 10,000 to 30,000 NSCs per microliter are used. In a preferred embodiment, the NSCs are concentrated to a density of about 70,000 NSCs per microliter.

In another embodiment, the NSCs are concentrated to a density of about 1,000 to about 10,000 cells per microliter, about 10,000 to about 20,000 cells per microliter, about 20,000 to about 30,000 cells per microliter, about 30,000 to about 40,000 cells per microliter, about 40,000 to about 50,000 cells per microliter, about 50,000 to about 60,000 cells per microliter, about 60,000 to about 70,000 cells per microliter, about 70,000 to about 80,000 cells per microliter, about 80,000 to about 90,000 cells per microliter, or about 90,000 to about 100,000 cells per microliter.

In another embodiment, the NSCs are concentrated to a density of about 100,000 to about 200,000 cells per microliter, about 200,000 to about 300,000 cells per microliter, about 300,000 to about 400,000 cells per microliter, about 400,000 to about 500,000 cells per microliter, about 500,000 to about 600,000 cells per microliter, about 600,000 to about 700,000 cells per microliter, about 700,000 to about 800,000 cells per microliter, about 800,000 to about 900,000 cells per microliter, about 900,000 to about 1,000,000 cells per microliter.

In another embodiment, the NSCs can be delivered to a treatment area suspended in an injection volume of less than about 100 microliters per injection site. For example, in the treatment of cognitive dysfunction of a human subject where multiple injections may be made, an injection volume of 0.1 and about 100 microliters per injection site can be used. In preferred embodiments, the NSCs can be delivered to a treatment area suspended in an injection volume of about 1 microliter per injection site.

In an embodiment, the disclosed methods include injecting NSCs at a cell density of about 1,000 to about 10,000 cells per microliter, about 10,000 to about 20,000 cells per microliter, about 20,000 to about 30,000 cells per microliter, about 30,000 to about 40,000 cells per microliter, about 40,000 to about 50,000 cells per microliter, about 50,000 to about 60,000 cells per microliter, about 60,000 to about 70,000 cells per microliter, about 70,000 to about 80,000 cells per microliter, about 80,000 to about 90,000 cells per microliter, or about 90,000 to about 100,000 cells per microliter into to one or more areas of the brain of the subject.

In some embodiments, the disclosed methods include injecting NSCs at a cell density of about 100,000 to about 200,000 cells per microliter, about 200,000 to about 300,000 cells per microliter, about 300,000 to about 400,000 cells per microliter, about 400,000 to about 500,000 cells per microliter, about 500,000 to about 600,000 cells per microliter, about 600,000 to about 700,000 cells per microliter, about 700,000 to about 800,000 cells per microliter, about 800,000 to about 900,000 cells per microliter, or about 900,000 to about 1,000,000 cells per microliter into to one or more areas of the brain of the subject.

In an embodiment, the disclosed methods include injecting NSCs at a cell density of about 5,000 to about 50,000 cells per microliter. In preferred embodiments, the disclosed methods include injecting NSCs at a cell density of about 70,000 cells per microliter.

In an embodiment, the disclosed methods include multiple injections of NSCs at a total cell number of about 4,000 to about 40,000 cells, about 40,000 to about 80,000 cells, about 80,000 to about 120,000 cells, about 120,000 to about 160,000 cells, about 160,000 to about 200,000 cells, about 200,000 to about 240,000 cells, about 240,000 to about 280,000 cells, about 280,000 to about 320,000 cells, about 320,000 to about 360,000 cells, or about 360,000 to about 400,000 cells introduced into one or more areas of the brain of the subject.

In some embodiments, the disclosed methods include multiple injections of NSCs with a total cell number of about 400,000 to about 800,000 cells, about 800,000 to about 1,200,000 cells, about 1,200,000 to about 1,600,000 cells, about 1,600,000 to about 2,000,000 cells, about 2,000,000 to about 2,400,000 cells, about 2,400,000 to about 2,800,000 cells, about 2,800,000 to about 3,200,000 cells, about 3,200,000 to about 3,600,000 cells, or about 3,600,000 to about 4,000,000 cells introduced into one or more areas of the brain of the subject.

The volume of media in which the expanded NSCs are suspended for delivery to a treatment area can be referred to herein as the injection volume. The injection volume depends upon the injection site and the degenerative state of the tissue. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

Any suitable device for injecting the cells into a desired area can be employed in the disclosed methods. In an embodiment, a syringe capable of delivering sub-microliter volumes over a time period at a substantially constant flow rate is used. The cells can be loaded into the device through a needle or flexible tubing or any other suitable transfer device.

In another embodiment, the cells are injected at between about 2 and about 5 sites in the brain. In an embodiment, the cells are injected at between about 5 and about 10 sites in the brain. In an embodiment, the cells are injected at between about 10 to about 30 sites in the brain. In an embodiment, the cells are injected at between about 10 to about 50 sites in the brain. At least two of the sites can be separated by a distance of approximately 100 microns to about 5,000 microns. In an embodiment, the distance between injection sites is about 400 to about 600 microns. In an embodiment, the distance between injections sites is about 100 to about 200 microns, about 200 to about 300 microns, about 300 to about 400 microns, about 400 to about 500 microns, about 500 to about 600 microns, about 600 to about 700 microns, about 700 to about 800 microns, about 800 to about 900 microns, or about 900 to about 1,000 microns. In an embodiment, the distance between injection sites is about 1,000 to about 2,000 microns, about 2,000 to about 3,000 microns, about 3,000 to about 4,000 microns, or about 4,000 to about 5,000 microns. The distance between injections sites can be determined based on generating substantially uninterrupted and contiguous donor cell presence throughout the spinal cord tissue and based on the average volume of injections demonstrated to achieve about 2-3 month survival in animal models such as rats or pigs. The actual number of injections and distance between injections in humans can be extrapolated from results in animal models.

The NSCs of the disclosed methods can generate large numbers of neurons in vivo. When the NSCs are not overtly pre-differentiated prior to transplant, the NSCs can proliferate up to two to four cell divisions in vivo before differentiating, thereby further increasing the number of effective donor cells. Upon differentiation, the neurons secrete specific neurotransmitters. In addition, the neurons secrete into the milieu surrounding the transplant in vivo growth factors, enzymes and other proteins or substances which are beneficial for different conditions. Accordingly, a variety of conditions can be treated by the disclosed methods because of the ability of the implanted cells to generate large numbers of neurons in vivo and because the cognitive dysfunction may be caused by or result in missing elements including neuron-derived elements. Therefore, subjects suffering from cognitive dysfunctions due to lack of such neuron-derived elements, such as growth factors, enzymes and other proteins, can be treated effectively by the disclosed methods.

In an embodiment, the composition comprising an amount of NSCs may be administered to a subject in accordance with known methods, such as intravenous administration, e.g., as a bolus or by continuous infusion over a period of time, by intramuscular, intraperitoneal, intracerebrospinal, intravenous, subcutaneous, intra-articular, intrasynovial, or intrathecal routes. Intracerebrospinal, intrathecal, intravenous, intraperitoneal, or subcutaneous administration of the cells is preferred, with intracerebrospinal, intrathecal, or intravenous routes being particularly preferred; however, other cell administration paradigms well known in the art can be used.

In one embodiment, compositions of the NSCs of the invention are formulated as an injectable formulation and comprise, for example, an aqueous solution or suspension of the active ingredient suitable for intracerebrospinal delivery. When preparing the composition for injection, particularly for intracerebral delivery, a continuous phase can be present that comprises an aqueous solution of tonicity modifiers, buffered to a pH below about 7, or below about 6, for example about 2 to about 7, about 3 to about 6 or about 3 to about 5. The tonicity modifiers can comprise, for example, sodium chloride, glucose, mannitol, trehalose, glycerol, or other pharmaceutical agents that render osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

In some embodiments of any of the aforementioned methods, the composition comprising NSCs is administered once. In some embodiments of any of the aforementioned methods, administration of an initial dose the composition comprising NSCs is followed by the administration of one or more subsequent doses. Examples of dosing regimens (e.g., an interval between the first dose and one or more subsequent doses) that can be used in the methods of the disclosure include an interval of about once every week to about once every 12 months, an interval of about once every two weeks to about once every 6 months, an interval of about once every month to about once every 6 months, an interval of about once every month to about once every 3 months, or an interval of about once every 3 months to about once every 6 months. In some embodiments, administration is monthly, every two months, every three months, every four months, every five months, every six months, or upon disease recurrence.

In an embodiment, the NSCs are injected at between about 5 and about 50 sites. In an embodiment, the NSCs are injected at between about 10 to about 30 sites. At least two of the sites can be separated by a distance of approximately 100 microns to about 5000 microns. In an embodiment, the distance between injection sites is about 400 to about 600 microns. The actual number of injections in humans can be extrapolated from results in animal models.

The methods of the present disclosure may include administration of one or more immunosuppressive drugs prior to, concurrent with, or after the injection of the NSCs.

In some embodiments, the NSCs and immunosuppressive drug may be co-administered. The NSCs and immunosuppressive drug which make up the therapy may be a combined dosage form or in separate dosage forms intended for substantially simultaneous administration. The NSCs and immunosuppressive drug may also be administered sequentially, with either the NSCs or immunosuppressive drug being administered by a regimen calling for multiple step administration. Thus, a regimen may call for sequential administration of the NSCs and immunosuppressive drug with spaced-apart administration of the separate, active agents. The time period between the multiple administration steps may range from, for example, a few minutes to several hours to days, depending upon the properties of the NSCs and immunosuppressive drug such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The NSCs and immunosuppressive drug whether administered simultaneously, substantially simultaneously, or sequentially, may involve a regimen calling for administration of the NSCs by intravenous route and the immunosuppressive drug by an oral route, a percutaneous route, an intravenous route, an intramuscular route, or by direct absorption through mucous membrane tissues, for example. Whether the neural stem cells and immunosuppressive drug are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

The present invention is further illustrated by the following examples, which should not be construed as limiting in any way. The materials and methods as used in the following experimental examples are described below.

Example 1: Materials and Methods

HK532 Preparation

The human HK532 NSC lines (NSI-HK532 and NSI-HK532.UbC-IGF-I) were provided by Neuralstem, Inc. (Rockville, Md.). Briefly, HK532 were prepared from cortical tissue obtained from a human fetus of 8-week gestational age following an elective abortion. The material was donated to Neuralstem, Inc. with informed consent in accordance with guidelines of the National Institutes of Health (NIH) and the FDA. Guidelines were reviewed and approved by an outside independent review board as described (Johe et al. (1996) Genes Dev. 10(24):3129-40). Cortical NSCs were conditionally immortalized using a retrovirus vector containing an immortalizing gene and the neomycin-resistance gene. The immortalizing gene comprised human c-myc cDNA fused at the 3' end with a cDNA fragment coding for the c-terminal ligand binding domain of human estrogen receptor. Cells were selected for neomycin resistance and propagated as a single cell line (HK532). The cell line was then transduced with a replication□defective recombinant lentiviral vector to induce expression of human IGF-I driven by the human ubiquitin C (UbC) promoter. Resulting cells were propagated as a single cell line without further selection (HK532.UbC-IGF-I). Transduction of HK532 using a control construct expressing green fluorescent protein (GFP) under the same UbC promoter yielded approximately 90-95% GFP-positive proliferating cells.

HK532 Culture and Differentiation

Culture of both HK532 and HK532-IGF-I cells was performed as previously described [42]. Briefly, cells were grown on flasks coated with 100 µg/mL poly-D-lysine (Millipore, Billerica, Mass.) in 10 mM Hepes buffer for 24 h, followed by 25 µg/mL fibronectin in PBS for 1 hour. Alternatively, cells were seeded on inserts coated with poly-L-lysine prior to co-culture with cortical neurons (CN). Cells were cultured in N2B+ media (supplied by Neuralstem, Inc., Rockville, Md.) supplemented with 10 ng/mL fibroblast growth factor (FGF) for progenitor state growth and maintenance. For differentiation, cells were cultured in NSDM differentiation media without FGF (DMEM supplemented with 4 mM L-glutamine, 20 µM L-alanine, 6 µM L-asparagine, 67 µM L-proline, 250 nM vitamin B12, 25 mg/L insulin, 100 mg/L transferrin, 20 nM progesterone, 100 µM putrescine, and 30 nM sodium selenite). Differentiated cell data are presented as days post-differentiation (i.e., undifferentiated (D0), day 1 (D1), day 3 (D3), etc.). Media was changed every 2 days with a 50% media change.

IGF-I Production and Signaling

IGF-I expression and signaling was determined in HK532 and HK532-IGF-I cells by ELISA and western blotting as previously described (Vincent et al. Endocrine Society Abstracts (2003) P3-316 p. 548; and Chia et al. Am J Epidemiol (2008) 167(12):1438-45). In brief, to confirm IGF-I production, conditioned medium was collected from undifferentiated (D0) and differentiated (D3 and D7) HK532 and HK532-IGF-I cells, concentrated 10 fold to 1 mL using Centricon filters (3 KDa cut off; Millipore, Billerica, Mass.), and run on a human-specific IGF-I ELISA (Assay Designs, Enzo Life Sciences Inc., Farmingdale, N.Y.) according to manufacturer's instructions. For IGF-I signaling analysis, HK532 and HK532-IGF-I cells were cultured in treatment medium (NSDM differentiation media without added insulin) for 4 hours prior to the addition of select inhibitors for 1 hour and subsequent addition of exogenous IGF-I (20 nM) for 30 min. Inhibitors included the Akt pathway inhibitor LY294002 (LY; 20 µM; Sigma-Aldrich, St. Louis, Mo.), the MAPK inhibitor U0126 (U; 20 µM; Calbiochem, La Jolla, Calif.) or the IGF-IR inhibitor NVPAEW541 (NVP; 1 µM; Sigma-Aldrich). For western blot, total cell protein was extracted in ice cold RIPA buffer (20 mM Tris, pH 7.4, 150 mM NaCl, 1 mM EDTA, 0.1% SDS, 1 mM Na deoxycholate, 1% Triton X-100, 0.1 trypsin units/L aprotinin, 10 mg/mL leupeptin, and 50 mg/mL PMSF), protein concentration was determined, and samples were electrophoresed on an SDS-PAGE gel and transferred to nitrocellulose. Primary antibodies (obtained from Cell Signaling Technology, Inc. (Danvers, Mass.) unless otherwise indicated)

included: phospho-IGF-IR (pIGF-IR), IGF-IRβ (Tyr1135/1136), phospho-Akt (Ser473) (pAkt), Akt, phospho-ERK (pERK), ERK, and β-actin (Chemicon, Temecula, Calif.). After overnight primary antibody incubation at 4° C., membranes were incubated with the appropriate secondary antibody conjugated to horseradish peroxidase (Cell Signaling Technology, Danvers, Mass.) for 1 hour at 22° C., developed with a chemiluminescent substrate (SuperSignal West Pico; Pierce, Fisher Scientific, Hampton, N.H.), and exposed to Kodak BioMax XAR film (Sigma-Aldrich).

Cellular Migration

Undifferentiated HK532 and HK532-IGF-I cells were added to migration inserts following overnight storage at 4° C. (1×106 cells/mL or 3×106 cells/vial), or were alternatively cultured on 6-well plates and moved to inserts on D7 of differentiation. NSDM plus 10% FBS with or without IGF-I (final concentration of 10 nM) was added below the inserts. After 24 hours, cells that had migrated through the insert were stained using the QCM 24-Well Colorimetric Cell Migration Assay (Millipore). Migration was quantified using a standard LabSystems Fluoroskan Ascent FL microplate reader at 530 and 590 nm.

Cellular Proliferation and Differentiation

Cellular proliferation and differentiation were assessed using standard laboratory immunocytochemistry (ICC) protocols (Kim et al. Journal of Biological Chemistry (1997) 272:21268-21273; Lunn et al. Neurobiol Dis (2012) 46(1): 59-68). Briefly, HK532 and HK532-IGF-I cells were cultured on poly-L-lysine and fibronectin-coated glass coverslips in 24-well plates. Cell proliferation was measured as previously described [45] at D0, D3, and D7 by incubating cells with 10 μM 5'-ethynyl-2'-deoxyuridine (EdU) for 2 hours prior to fixation and processing following the manufacturers' protocols for the Click-It EdU kit (Invitrogen). EdU incorporation was measured by quantification of fluorescent images captured using an Olympus BX-51 microscope equipped with a digital camera. Approximately 2.5-2.7×103 cells were counted per proliferation experiment for all samples (n=3).

To assess differentiation, cells were fixed with 4% PFA, permeabilized with 0.1% Triton/PBS, and blocked in 5% normal donkey serum/0.1% Triton/PBS. Next, Ki67 (Novus, Littleton, Colo.), TUJ1 (Neuromics, Edina, Minn.), Nestin (Chemicon, Millipore), GAD65/67 (Millipore), VGLUT2 (Millipore), or IGF-IR13 (1:500, Sigma) primary antibodies were incubated at 1:1000, unless otherwise indicated, overnight at 4° C. Cells were then incubated in Cy3, Cy5, or FITC-conjugated secondary antibodies (Jackson ImmunoResearch, Westgrove, Pa.) followed by mounting on glass slides using ProLong Gold anti-fade with DAPI (Molecular Probes, Invitrogen, Carlsbad, Calif.). Images were captured using an Olympus BX-51 microscope and approximately 2.5-2.7×103 cells were counted per differentiation experiment for all samples (n=3).

We next examined the effect of induced IGF-I expression on the maintenance of progenitor status and axonal outgrowth using our established neural index measurement as previously described (Lunn et al. Stem Cells Dev (2010) 19(12):1983-93). Briefly, cells were cultured in a monolayer on glass coverslips for the first 7 days of differentiation and immunolabeled at D0, D3, and D7 with Nestin to identify neural progenitors or with TUJ1 to observe primary neuronal processes. Over 2.5×103 cells were counted per experiment for all Nestin-labeled samples (n=3). Alternatively, TUJ1-labeled images and their corresponding DAPI images were analyzed using MetaMorph (Molecular Devices, Sunnyvale, Calif.). Thresholds were set and the area covered by neurites was measured using region statistics. Cell number was counted using the "count nuclei" plug-in and manual adjustment was made to correct for any miscounted cells. The number of neurons and neurite length were analyzed using a composite neural index measurement, which is expressed as the complete neuronal area divided by the number of nuclei. Data are presented as neurite area per cell (μm2/cell) (Lunn et al. Stem Cells Dev (2010) 19(12): 1983-93). A total of 6 images per condition were counted representing approximately 7.5×103 DAPI-labeled cells (n=3).

Primary CN Preparation and Assessment of Neuroprotection

Primary CN were isolated according to our previously published protocol (Lunn et al. Stem Cells Dev (2010) 19(12):1983-93). Briefly, CN from E15 Sprague-Dawley rat embryos were collected, membranes were removed, and the tissue was chopped into 2-3 mm pieces. Cells were dissociated by incubating the tissue in 0.5% trypsin/EDTA for 10 minutes at 37° C. followed by trituration with a serum-coated glass pipette for 1 minute. The resulting cell suspension was applied to poly-L-lysine-coated glass coverslips in a 24-well plate and incubated in growth medium, which comprised Neurobasal Medium (Gibco BRL, Invitrogen) supplemented with 2.5 mg/ml albumin, 2.5 μg/ml catalase, 2.5 μg/ml SOD, 0.01 mg/ml transferrin, 15 μg/ml galactose, 6.3 ng/ml progesterone, 16 μg/ml putrescine, 4 ng/ml selenium, 3 ng/ml β-estradiol, 4 ng/ml hydrocortisone, 1× penicillin/streptomycin/neomycin (Gibco BRL), and 1×B-27 additives (Gibco BRL).

To examine CN, HK532 and HK532-IGF-I susceptibility to the toxic AD microenvironment, cells were treated with 10 μM Aβ (1-42) (rPeptide) for approximately 72 hours. Cellular injury was assessed by cleaved caspase-3 activation (CC3), determined by counting the percentage of CC3-positive cells following ICC. Approximately 2.5×103 cells were counted per experiment for all samples (n=3). To assess neuroprotective effects, differentiated D7 HK532-IGF-I were seeded on inserts and co-cultured with primary CN cultures in regular growth medium. After 24 hours, co-cultures were treated with 10 βM Aβ (1-42) (rPeptide) for 72 hours. Primary CN were fixed for ICC analysis as described above using a CC3 antibody (1:1000, Cell Signaling).

In Vivo Transplantation

To demonstrate that HK532-IGF-I cells survive and integrate into the hippocampal region following in vivo transplantation, B6C3-Tg (APPswe/PSENΔ1E9)85Dbo/J (APP/PS1; n=5) and wild type B6C3F1/J (WT; n=8) mice were obtained from the Jackson Laboratory (Bar Harbor, Me.) at 6 weeks of age. At 11 weeks of age, mice received subcutaneous Tacrolimus pellets (FK-506; supplied by Neuralstem, Inc.) and cell transplantation surgery was performed at 12 weeks of age. Briefly, mice were anesthetized with isofluorane and placed in a standard stereotactic frame (Stoelting Company, Wood Dale, Ill.). Skin was incised and a large craniotomy was performed at the area of predicted injections. HK532-IGF-I cell suspensions were administered by bilateral injections into the fimbria fornix at 3 sites (total 6 injections) represented by the following coordinates measured from the bregma (posterior/lateral/ventral, respectively): −0.82/±0.75/2.5, −1.46/±2.3/2.9, −1.94/±2.8/2.9. Each injection consisted of 1 μL volume (administered over 60 sec, with a 60 sec delay prior to needle withdrawal) at a cell concentration of 30,000 cells/μL. Skin was then closed using absorbable sutures. Postoperatively, mice were given intraperitoneal narcotic pain medications for 2 days and Tacrolimus pellets were continued throughout the study.

Mice were sacrificed at 2 and 10 weeks post-cell transplantation for analysis. Briefly, animals were anaesthetized and perfused with ice-cold saline and brains were dissected and cut along the interhemispheric boundary. Brains were post-fixed in 4% PFA overnight and cryoprotected in 30% sucrose for immunohistochemistry (IHC).

For IHC, fixed brain tissue was embedded using Optimal Cutting Temperature compound (OCT) and sectioned into 14 μm slices using a cryostat. Ten sections of the hippocampus per animal were selected for IHC to detect grafted cells and verify accurate targeting to the fimbria fornix. Sections were rehydrated in PBS, permeabilized in 0.5% Triton X-100 in PBS for 20 minutes, and blocked in 5% donkey serum in 0.1% Triton X-100 in 1×PBS for 30 min. Primary antibodies for Doublecortin (DCX; Millipore) and Human Nuclei (HuNu; Millipore) were diluted 1:200 in block and incubated with sections overnight at 4° C. After primary antibody incubation, sections were washed 3× in PBS and incubated for 1 hour with fluorescent-conjugated secondary antibodies raised in donkey (Alexa 488 and Alexa 594; 1:500; Invitrogen). Once staining was complete, slides were mounted with glass coverslips using ProLong Gold anti-fade mounting medium containing DAPI nuclear stain (Molecular Probes, Invitrogen). Fluorescent images were captured using a Leica SP2 confocal microscope.

Statistical Analyses

All data are presented as mean±standard deviation (SD), n=3, or as representative images of three independent experiments. Statistical analysis was performed using GraphPad Prism (GraphPad Software, Inc., La Jolla, Calif.). Paired t-tests were used for pairwise comparisons. Values of $p<0.05$ were considered statistically significant (*$p<0.05$).

Example 2: IGF-I Production and Signaling

HK532 cells are novel cortical NSCs that have not been previously described. To enhance their potential efficacy as a cellular therapeutic and to determine the impact of IGF-I production on their neuroprotective capacity, a lentivirus vector encoding full length human IGF□I was used to generate the HK532-IGF-I cell line. ELISA analysis of conditioned medium demonstrated that parental HK532 cells produce very low to undetectable basal levels of IGF-I, whereas HK532-IGF-I cells produce 3-5 ng/mL of IGF-I between D0 and D7, approximately a 50-fold increase (FIG. 1 A). Thus, HK532-IGF-I cells produce appreciable levels of IGF-I which are maintained throughout early differentiation, confirming robust and stable IGF-I expression.

An examination of how growth factor receptor level and activation are regulated by autocrine IGF□I expression was conducted. By IHC, IGF□IR expression was observed along the cell surface of both parental HK532 cells and HK532-IGF-I at D7 (FIG. 1 B). Western blot analysis confirmed this expression and also revealed a significant increase in receptor expression after differentiation in both cell lines (FIG. 1 C). Although slightly reduced IGF-IR expression levels were observed in HK532-IGF-I relative to HK532 at D0 and D7, IGF-IR phosphorylation and signaling activation did not significantly differ between cell lines and addition of exogenous IGF-I resulted in increased phosphorylation of the receptor (FIG. 1 C); this activation was significantly more pronounced after differentiation.

Given that IGF-I signaling activates the mitogen-activated extracellular signal-regulated kinase/extracellular signal-regulated kinase (MEK/ERK), mitogen-activated protein kinase (MAPK) and phosphatidylinositol 3-kinase (PI3K)/Akt pathways, phosphorylation and downstream activation of these key pathways was assessed in HK532 and HK532-IGF-I cells (FIG. 1 C). While basal MAPK signaling was present at D0 and D7, there were no significant differences between cell lines and IGF-I stimulation only increased signaling after differentiation. Basal Akt signaling, however, was significantly increased in D0 HK532-IGF-I cells and in both cell lines after differentiation. Addition of exogenous IGF-I promoted a robust increase in Akt in HK532 cells after differentiation while very little Akt activation was observed following IGF-I stimulation in HK532-IGF-I. These data demonstrate a decreased responsiveness of HK532-IGF-I to exogenous IGF-I relative to parental cells. Notably, inhibition of MAPK signaling increased Akt phosphorylation and inhibition of Akt signaling resulted in the reverse observation, suggesting that these pathways are capable of compensatory signaling. Inhibition of IGF-IR signaling using the receptor antagonist NVP, however, did not affect MAPK signaling but did significantly deplete activation of IGF-IR and Akt to below basal levels in both cell lines (FIG. 1 C). Together, these data demonstrate that HK532-IGF-I cells exhibit normal IGF-IR and MAPK/Akt signaling profiles.

Example 3: IGF-I Expression Does Not Alter HK532 Proliferation or Migration

EdU incorporation was used to assess the effect of IGF-I on HK532 and HK532-IGF-I cell proliferation. Approximately 36% and 33% of untreated D0 HK532 and HK532-IGF-I were EdU-positive, respectively (FIG. 2 A-E). At D3, 6% and 9% of HK532 and HK532-IGF-I were EdU-positive, respectively, and by D7, less than 3% of either cell line were EdU-positive. Thus, no differences in the proliferation profiles were observed at D0, D3, or D7, and both lines exhibited minimal proliferation at D7. These data demonstrate that IGF-I does not promote or maintain proliferation during the initial stages of differentiation.

The effect of IGF-I on HK532 and HK532-IGF-I migration was also assessed at D0 and D7. Comparable migration levels were observed for HK532 and HK532-IGF-I at both time points (FIG. 2 F-G). Furthermore, when additional IGF-I was added below transwell inserts, no change was observed. Thus, induced IGF-I expression exerted no discernable effects on progenitor cell migration.

Example 4: IGF-I-Expressing HK532 Retain Neural Differentiation Capacity

Next, the effect of IGF-I on the maintenance of HK532 progenitor status and axonal outgrowth was examined. Approximately 92% and 90% of D0 HK532 and HK532-IGF-I were Nestin-positive, respectively, indicating that IGF-I expression did not affect the maintenance of progenitor status. The effect of IGF-I on neurite outgrowth using an established neural index approach as an early indicator of neuronal differentiation was also assessed. For both HK532 and HK532-IGF-I cells, the neural index increased between D0 and D7 as the cells differentiated, and no differences were observed between the cell lines at any time point tested (FIG. 3 F). These data demonstrate that IGF-I does not affect initial HK532 differentiation.

Example 5: GABAergic but Not Glutamatergic Phenotypes are Increased in HK532-IGF-I To determine the effect of IGF-I on terminal differentiation, the proportion of cells exhibiting glutamatergic (VGLUT) and GABAergic (GAD65) phenotypes at D0, D3, and D7. GAD65-positive cells were quantified and were significantly increased in HK532-IGF-I compared to the parental HK532 cells, at 74% and 67% of the total cells, respectively (FIG. 4 A, B, E). The percentage of VGLUT-positive cells in HK532 (61%) and HK532-IGF-I (67%) cultures were not significantly different (FIG. 4 C, D, F). These data demonstrate that the presence of IGF-I increases the number of GABAergic neurons resulting from cell differentiation, but has no significant effect on the number of glutamatergic neurons.

Example 6: HK532-IGF-I are Resistant to Aβ Toxicity and Protect Primary CN In Vitro Aβ (1-42) is a commonly used in vitro model of AD-associated toxicity (Bruce et al. (1996) PNAS 93(6):2312-6). Significant apoptosis and CC3 activation was observed in primary CN and both NSC lines when exposed to Aβ (FIG. 5 A). Apoptosis levels in HK532 and HK532-IGF-I were significantly lower than that observed in primary CN (p<0.05; FIG. 5 A). To examine the protective capacity of the modified progenitors, Aβ toxicity was also assessed in primary CN indirectly co-cultured with HK532 and HK532-IGF-I (FIG. 5 B-E). Apoptosis in primary CN, again indicated by CC3 activation, was significantly decreased to below 40% when co-cultured with HK532 and to below 30%, when co-cultured with HK532-IGF-I, (p<0.05; FIG. 5 F). These data indicate the HK532-IGF-I cell line is neuroprotective and capable of preventing Aβ-induced primary CN death.

Example 7: HK532-IGF-I Survive Transplantation and Incorporate In Vivo in an AD Mouse Model To establish the feasibility of preclinical testing, HK532-IGF-I cells were transplanted into APP/PS1 double transgenic mice, a commonly used model of AD (Cao et al. J Biol Chem (2007) 282(50):36275-82). This pilot study served to confirm accurate and correct anatomical placement of the cells in the fimbria fornix of the hippocampus and assess transplanted cell survival over time. Targeting accuracy was achieved in all animals injected. Transplanted human cells were detected by IHC for HuNu and DCX at 2 weeks (data not shown) and at 10 weeks post-transplantation (FIG. 5 E, F). Grafted cells were evident in the hippocampal regions of both AD (FIG. 5 E) and WT animals (FIG. 6 F). Co-staining of HuNu-labeled cells with DCX, a microtubule-associated phosphoprotein that labels neuronal precursors, is indicative of neurogenesis and suggests that transplanted cortical progenitors were in an early neuronal differentiation phase.

Example 8: Administration of HK532-IGF-I Reduces Aβ Plaque Formation In Vivo in an AD Mouse Model In order to evaluate the global effects of in vivo HK532-IGF-I transplantation on Aβ pathology, immunostaining was performed on multiple hippocampal and cortical sections per mouse with a polyclonal antibody against five Aβ isoforms (Aβ-37, 38, 39, 40, and 42). Fluorescent images of sections were quantified based on measures of total immunoreactive area and intensity. As expected, the results show clear Aβ plaque formation in vehicle-injected APP/PS1 mice and an absence of Aβ in non-tg animals (FIG. 6A-B, D-E). Moreover, there was a largely significant reduction in Aβ levels in APP/PS1 mice treated with HK532-IGF-I compared with vehicle-injected APP/PS1 mice (P<0.0001; unpaired t-test) (FIG. 6B-C, E-G). This data shows that HK532-IGF-I not only functions to protect neuronal tissue from Aβ-induced damage, but attenuates the deposition of Aβ by clearing Aβ deposits and/or resisting Aβ accumulation.

To gain more insight on the mechanism of Aβ reduction in the NSC-treated mice, the differences in Aβ levels in the hippocampus and cortex were separately considered. Aβ was significantly reduced in the cortex of NSC-treated mice (P<0.0005; unpaired t-test) (FIG. 6H). However, the reduction of Aβ in the hippocampus of NSC-treated mice was not significant (P=0.1061; unpaired t-test) (FIG. 6H).

Figure 7A:
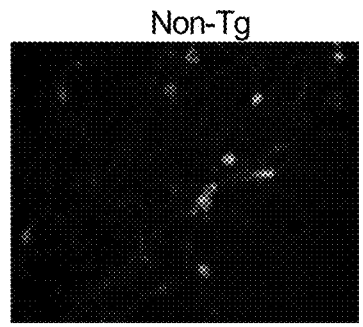
FIG. 7A-F. HK532-IGF-I engraftment rescues cholinergic neurons in the striatum. (A-C) Fluorescent images of the striatum immunostained for ChAT (green) in each group. Scale Bar 100 µm. (D) High magnification image of ChAT positive cell. Nuclei were stained with DAPI (blue). Scale Bar: 50 µm (E) Cell counts throughout the striata of all mice revealed a significant loss of cholinergic neurons in vehicle-injected APP/PSI mice compared to non-tg mice. *P<0.05. (F) Calculation of fold change in cholinergic neurons from non-tg mice reveal a significantly higher quantity in APP/PSI mice treated with HK532-IGF-I. *P<0.05
Figure 7B:
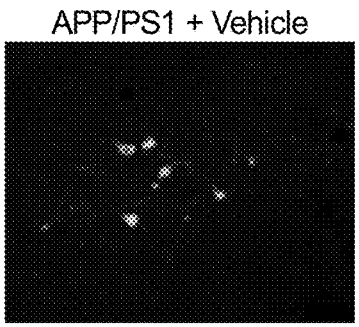
Figure 7C:
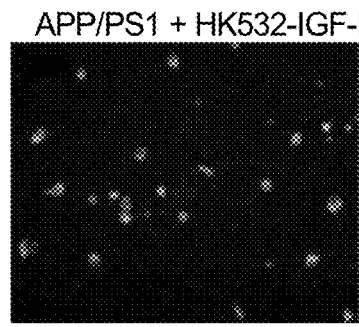
Figure 7D:
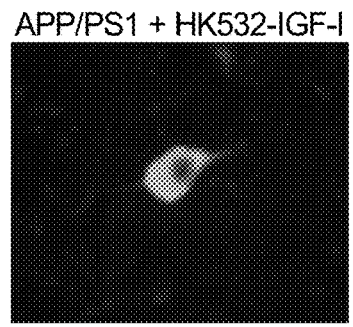
Figure 7E:
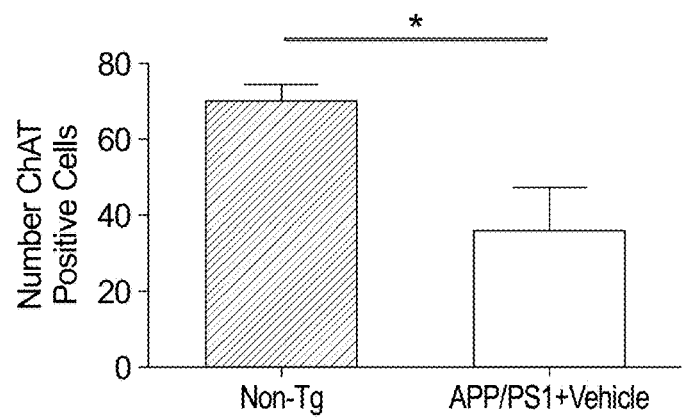
Figure 7F:
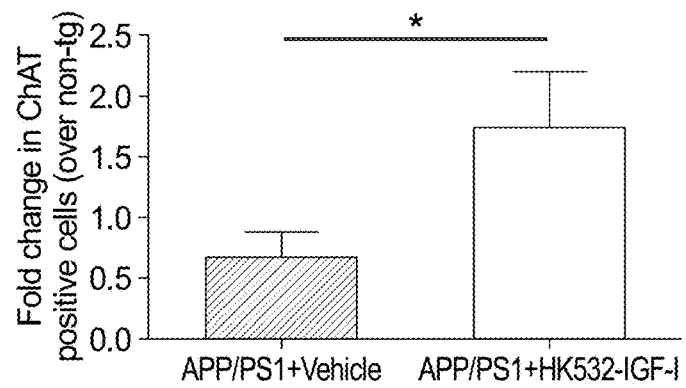

Example 9: Administration of HK532-IGF-I Increases Cholinergic Activity In Vivo in an AD Mouse Model To assess the presence of cholinergic neurons in our AD model and investigate the effects of HK532-IGF-I transplantation on these neurons, striatal sections from each mouse were immunostained with antibodies against ChAT to identify cholinergic neurons expressing intense levels of ChAT (FIG. 7A-D). We imaged the entirety of the striatum for each section and counted the number of ChAT-positive cells for each. Cell counts indicated a significant loss of striatal cholinergic neurons in APP/PS1 mice compared to the WT (P=0.0115; unpaired t-test) (FIG. 7E). Furthermore, there was a significant increase in the number of cholinergic neurons in NSC-treated APP/PS1 mice compared to vehicle-injected AD mice (P=0.0366; unpaired t-test) (FIG. 7F). These results indicate rescue of cholinergic function in the striatum by HK532-IGF-I transplantation in the APP/PS1 mice.

Example 10: Administration of HK532-IGF-I Increases Pre-Synaptic Activity In Vivo in an AD Mouse Model In order to determine if HK532-IGF-I increases the synaptic density in the APP/PS1 mouse, hippocampal sections were immunostained from all animals with the pre-synaptic marker, synaptophysin. A discernable increase was found in the fluorescence intensity at the hippocampus of APP/PS1 mice transplanted with HK532-IGF-I compared to the vehicle-injected transgenic mice (FIG. 8A-F). This increased intensity was comparable to the levels found in both the un-injected and sham treated non-tg mice. These data indicate that HK532-IGF-I transplantation rescues memory and cognition by restoring synapses in AD.

Figure 8A:
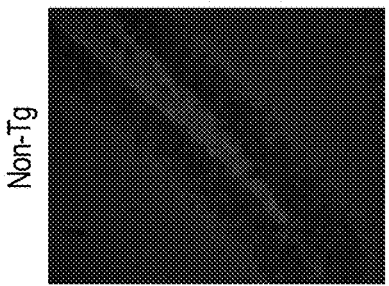
FIG. 8A-J. HK532-IGF-I increases pre-synaptic activity and forms synapses with endogenous neurons. (A-C) Fluorescence microscopy of hippocampal sections stained for synaptophysin reveal a visibly increased intensity of fluorescent signal in non-tg and NSC-injected APP/PSI mice compared to vehicle-injected APP/PSI mice. Scale Bar: 100 µm. (D-F) High magnification images of synaptophysin near the granule cell layer of dentate gyrus. Scale Bar: 50 µm. (G-J) Fluorescent images of sections from NSC-treated group immunostained for human NuMA (red), synaptophysin (green) and DAPI (blue), showing pre-synaptic function surrounding NSCs. Scale Bar: 50 µm.
Figure 8D:
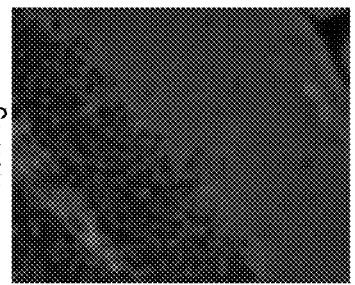
Figure 8B:
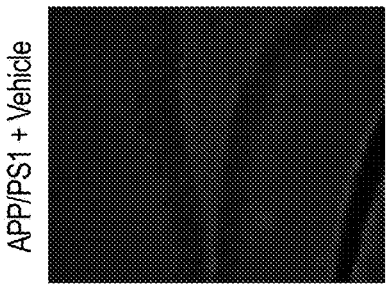
Figure 8E:
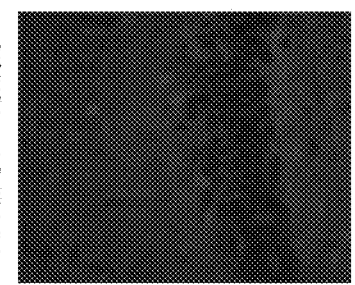
Figure 8C:
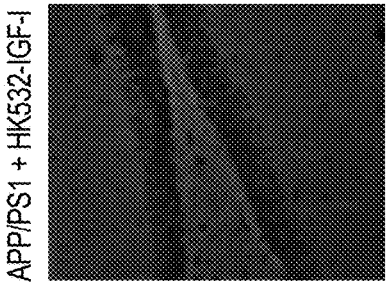
Figure 8F:
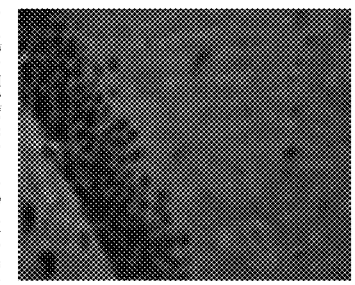
Figure 8G:
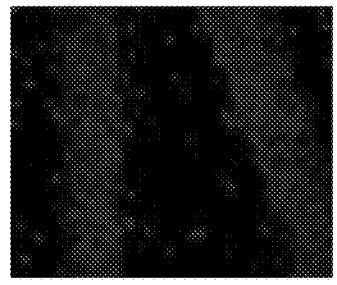
Figure 8H:
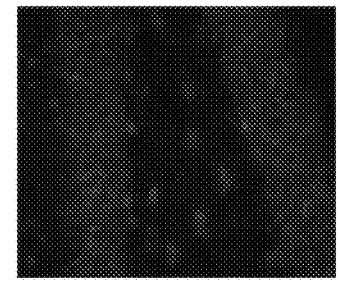
Figure 8I:
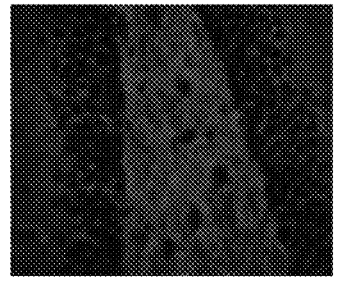
Figure 8J:
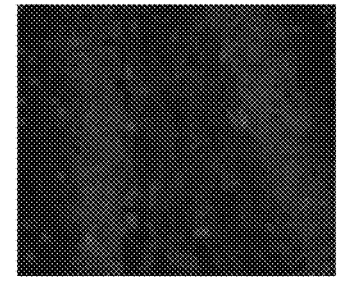

To investigate whether or not HK532-IGF-I cells were forming synapses with endogenous neurons, co-staining for human NuMA and synaptophysin of both mouse and human origin was performed on hippocampal sections of HK532-IGF-I treated mice. Considerable synaptophysin-positive staining was found in the areas of the polymorph layer in which NSCs were located (FIG. 8I). Moreover, the synaptic markers distinctly bordered the NuMA-stained cells (FIG. 8G-J) suggesting that human NSC-derived cells can form synapses with endogenous neurons.

Example 11: Survival and Integration of HK532.UbC-IGF1 in Spinal Cord

In order to demonstrate survival and integration into the spinal cord, HK532.UbC-IGF1 was transplanted into the cervical spinal cord of SOD1G93A rats, an established animal model of Amyotrophic Lateral Sclerosis (ALS). A total of 1.8×105 cells were injected into each animal, targeting the ventral horn of the cervical spinal cord (C4-C6 spinal levels). Animals were immunosuppressed by transient mycophenolate mofetil (30 mg/kg IP for 7 d post-grafting) and by continuous tacrolimus delivery. Animals survived 56 d before standard perfusion-fixation. Frozen-immunohistochemistry reveals the presence of human cell grafts in the ventral horn and a wide distribution throughout the gray- and white-matter (FIGS. 9A, 9A', 9A", 9B and 9C).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A stable human neural stem cell comprising a vector containing an exogenous polynucleotide coding for insulin-like growth factor 1 (IGF-1) isoform 4 wherein the human neural stem cell is expandable for more than sixty cell doublings without undergoing differentiation.

2. The human neural stem cell of claim 1, wherein the human neural stem cell is derived from tissue selected from the group consisting of: cortex, hippocampus, thalamus, midbrain, cerebellum, hindbrain, spinal cord, and dorsal root ganglia.

* * * * *

SEQUENCE LISTING

<160> NUMBER OF SEQ ID NOS: 3

<210> SEQ ID NO 1
<211> LENGTH: 477
<212> TYPE: DNA
<213> ORGANISM: Artificial sequence
<220> FEATURE:
<223> OTHER INFORMATION: Synthesized: IGF-1 isoform 4 cDNA

<400> SEQUENCE: 1

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca cccctcaagc ctgccaagtc agctcgctct     360
gtccgtgccc agcgccacac cgacatgccc aagacccaga agtatcagcc ccatctacc      420 aacaagaaca cgaagtctca gagaaggaaa ggaagtacat ttgaagaacg caagtag       477
```

<210> SEQ ID NO 2
<211> LENGTH: 158
<212> TYPE: PRT
<213> ORGANISM: Artificial sequence
<220> FEATURE:
<223> OTHER INFORMATION: Synthesized: IGF-1 isoform 4 protein

<400> SEQUENCE: 2

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155
```

<210> SEQ ID NO 3
<211> LENGTH: 1217
<212> TYPE: DNA
<213> ORGANISM: Artificial sequence
<220> FEATURE:
<223> OTHER INFORMATION: Synthesized: human ubiquitin C promoter

<400> SEQUENCE: 3

```
gatctggcct ccgcgccggg ttttggcgcc tcccgcgggc gcccccctcc tcacggcgag     60
cgctgccacg tcagacgaag ggcgcagcga gcgtcctgat ccttccgccc ggacgctcag    120
gacagcggcc cgctgctcat aagactcggc cttagaaccc cagtatcagc agaaggacat    180
tttaggacgg gacttgggtg actctagggc actggttttc tttccagaga gcggaacagg    240
cgaggaaaag tagtcccttc tcggcgattc tgcggaggga tctccgtggg gcggtgaacg    300
ccgatgatta tataaggacg cgccgggtgt ggcacagcta gttccgtcgc agccgggatt    360
```

```
tgggtcgcgg ttcttgtttg tggatcgctg tgatcgtcac ttggtgagta gcgggctgct      420
gggctggccg gggctttcgt ggccgccggg ccgctcggtg ggacggaagc gtgtggagag      480
accgccaagg gctgtagtct gggtccgcga gcaaggttgc cctgaactgg gggttggggg      540
gagcgcagca aaatggcggc tgttcccgag tcttgaatgg aagacgcttg tgaggcgggc      600
tgtgaggtcg ttgaaacaag gtggggggca tggtgggcgg caagaaccca aggtcttgag      660
gccttcgcta atgcgggaaa gctcttattc gggtgagatg ggctggggca ccatctgggg      720
accctgacgt gaagtttgtc actgactgga gaactcgggt ttgtcgtctg gttgcggggg      780
cggcagttat gcggtgccgt tgggcagtgc acccgtacct ttgggagcgc gcgcctcgtc      840
gtgtcgtgac gtcacccgtt ctgttggctt ataatgcagg gtggggccac ctgccggtag      900
gtgtgcggta ggcttttctc cgtcgcagga cgcagggttc gggcctaggg taggctctcc      960
tgaatcgaca ggcgccggac ctctggtgag gggagggata agtgaggcgt cagtttcttt     1020
ggtcggtttt atgtacctat cttcttaagt agctgaagct ccggttttga actatgcgct     1080
cggggttggc gagtgtgttt tgtgaagttt tttaggcacc ttttgaaatg taatcatttg     1140
ggtcaatatg taattttcag tgttagacta gtaaattgtc cgctaaattc tggccgtttt     1200
tggctttttt gttagac                                                    1217
```